(12) United States Patent
Meissonnier et al.

(10) Patent No.: US 9,259,389 B2
(45) Date of Patent: Feb. 16, 2016

(54) PHARMACEUTICAL ORAL DOSAGE FORM CONTAINING A SYNTHETIC OLIGOSACCHARIDE

(75) Inventors: Julien Meissonnier, La Wantzenau (FR); Nathalie Sicre, Haguenau (FR); Guillaume Sabate, Roeschwoog (FR); Guy Dubreucq, Lille (FR); Vanessa Nancy-Portebois, Les Pavillons-Sous-Bois (FR); Maurice Petitou, Paris (FR)

(73) Assignees: ENDOTIS PHARMA, Loos (FR); CATALENT FRANCE BEINHEIM SA, Beinheim (FR)

(*) Notice: Subject to any disclaimer, the term of this patent is extended or adjusted under 35 U.S.C. 154(b) by 435 days.

(21) Appl. No.: 13/515,965

(22) PCT Filed: Dec. 17, 2010

(86) PCT No.: PCT/EP2010/070117
§ 371 (c)(1),
(2), (4) Date: Jun. 14, 2012

(87) PCT Pub. No.: WO2011/073408
PCT Pub. Date: Jun. 23, 2011

(65) Prior Publication Data
US 2012/0316132 A1    Dec. 13, 2012

(30) Foreign Application Priority Data
Dec. 18, 2009   (EP) ..................................... 09306271

(51) Int. Cl.
 *A61K 31/70*   (2006.01)
 *A61K 9/107*   (2006.01)
 *A61K 9/48*    (2006.01)
 *A61K 31/702*  (2006.01)

(52) U.S. Cl.
 CPC ............... *A61K 9/107* (2013.01); *A61K 9/4891* (2013.01); *A61K 31/702* (2013.01)

(58) Field of Classification Search
 CPC .............................. A61K 9/107; A61K 31/702
 USPC .......................................................... 514/56
 See application file for complete search history.

(56) References Cited

U.S. PATENT DOCUMENTS

| 5,626,869 A | 5/1997 | Nyqvist et al. |
| 2002/0032171 A1 | 3/2002 | Chen et al. |
| 2005/0080042 A1* | 4/2005 | Seifert et al. .................... 514/56 |

FOREIGN PATENT DOCUMENTS

WO    WO 02/053100 A2    7/2002

OTHER PUBLICATIONS

Lyons et al., "Factors limiting the oral bioavailability of N-acetylglucosaminyl-N-acetylmuramyl dipeptide (GMDP) and enhancement of absorption in rats by delivery in a water-in-oil microemulsion," International Journal of Pharmaceutics, vol. 199, No. 1, pp. 17-28, Apr. 10, 2000.
Kim et al., "Tricaprylin microemulsion for oral delivery of low molecular weight heparin conjugates," Journal of Controlled Release, vol. 105, No. 1-2, pp. 32-42, Jun. 20, 2005.
Kibbe, ed., "Collodial Silicon Dioxide," Handbook of Pharmaceutical Excipients, pp. 143-145, Dec. 31, 2000.
International Search Report issued in application No. PCT/EP2010/070117 on Jan. 24, 2012.

* cited by examiner

*Primary Examiner* — Elli Peselev
(74) *Attorney, Agent, or Firm* — Foley & Lardner LLP

(57) ABSTRACT

The present invention concerns a pharmaceutical formulation intended for oral administration containing a synthetic oligosaccharides containing one to 18 monosaccharide units and having a therapeutical activity or a pharmaceutically acceptable additions salt or solvate thereof wherein the formulation contains: a) the synthetic oligosaccharide (A) in an amount of up to 5% by weight of the total weight of the formulation, advantageously up to 1% by weight of the total weight of the formulation, b), a lipophilic phase (B) consisting of triglyceride of fatty acids in an amount of 50 to 80% by weight of the total weight of the formulation, advantageously of 50 to 70% by weight of the total weight of the formulation, c) at least one lipophilic surfactant (C) with HLB below 7 consisting of partial esters of polyol and fatty acids in an amount of 10 to 30% by weight of the total weight of the formulation, advantageously of 15 to 30% by weight of the total weight of the formulation, d) at least one hydrophilic surfactant (D) with HLB above 7 in an amount of up to 20% by weight of the total weight of the formulation, advantageously up to 15% by weight of the total weight of the formulation, e) optionally, at least one hydrophilic solvent (E) in an amount of up to 15% by weight of the total weight of the formulation, advantageously up to 10% by weight of the total weight of the formulation, (F) between 0 and 30% by weight of the total weight of the formulation of a chemical and/or physical stabilization agent (F), advantageously between 0 and 20% by weight of the total weight of the formulation, wherein when the formulation is in a form of a reverse emulsion or microemulsion and contains at least one hydrophilic solvent (E), the physical stabilization agent is present and is silicon dioxide.

19 Claims, No Drawings

PHARMACEUTICAL ORAL DOSAGE FORM CONTAINING A SYNTHETIC OLIGOSACCHARIDE

The present invention relates to pharmaceutical formulation intended for oral administration containing a synthetic oligosaccharide having a therapeutical activity.

Synthetic oligosaccharides, in particular heparin-related pentasaccharides, are well-known compounds having pharmaceutical properties, such as antithrombotic activity. However, they can only be administered intravenously or subcutaneously because they can not cross the intestinal barrier. This considerably restricts their clinical use. Therefore, it would be highly advisable to render all these oligosaccharides orally absorbable.

Attempts have been made to increase the enteric absorbability with use of non-ionic surfactants only, as indicated in U.S. Pat. No. 4,656,161. However, the presence of a too high amount of surfactants can be toxic for the patient. Furthermore, when using synthetic oligosaccharides instead of heparin, the inventors have surprisingly found that the nature of the surfactant is of limited interest for the enteric absorbability and that the surfactant can not be used alone in order to increase the enteric absorbability in rat and therefore the oral absorbability.

The U.S. Pat. No. 5,714,477 has disclosed the use of glycerol esters of fatty acids in order to enhance the absorption of heparins through body membranes. In particular mono and di-glycerides are particularly preferred when compared to triglycerides (column 3 lines 25-31 and example 1).

U.S. Pat. No. 5,626,869 discloses pharmaceutical compositions containing a defined lipid system, in which at least one of the lipid component is amphiphatic and polar and one is nonpolar, to administer heparin orally, rectally, or transdermally. In particular, the polar lipid is phosphatidylcholine and the nonpolar lipid is a monoglyceride.

WO 02/053100 discloses a low molecular weight heparin formulation with at least one hydrophilic or hydrophobic surfactant or mixtures thereof, a bile salt or bile acid, and a means for delayed release. In particular, the composition is optically clear and substantially triglyceride-free.

However, the inventors have surprisingly found that in order to improve the enteric absorbability and therefore the oral absorbability of synthetic oligosaccharides, the presence of triglyceride in a particular amount, in admixture with partial esters of polyol and fatty acids, is necessary.

Kim S. K. et al. (2005) have developed a microemulsion for oral delivery of low molecular weight heparin conjugates in mice and monkeys. A LMWH is chemically conjugated to deoxycholic acid (DOCA) to facilitate intestinal absorption, and mixed with a triglyceride, water and non-ionic surfactants. However, the inventors have discovered that such surfactants can have a negative impact on the digestibility of the formulation when present above a certain amount. In addition, the inventors have observed that a high amount of synthetic oligosaccharide is not desirable as it affects negatively the physical oral bioavailability of the oligosaccharide.

U.S. Pat. No. 6,761,903 discloses particular pharmaceutical compositions capable of increasing the rate and/or the extent of bioabsorption of co-administered therapeutic agent such as heparin. Such a composition contains a carrier which includes a triglyceride and at least two surfactants, one of which being hydrophilic and the other one hydrophobic. A long list of these surfactants is indicated in this document, without pointing particularly to a particular mixture. The only other important characteristic of this composition is that it must be clear, i.e. it must have a particular absorbance property.

However the inventors have surprisingly found that the absorbance property has no impact on the extent of absorption after oral delivery and that only particular hydrophobic surfactants in a particular amount can be used in order to obtain a pharmaceutical composition containing a synthetic oligosaccharide having a good oral bioavailability.

Lyons K. C. et al. (2000) have developed a reverse microemulsion to enhance the oral bioavailability of a non-heparinic oligosaccharide (GMDP). The microemulsion contains an aqueous phase, a caprylic/capric triglyceride, mono- and diglyceride of caprylic acid, as well as polyoxythylene-sorbitan monooleate. However, this formulation has only been administered intra-duodenally to rats but not orally. In addition, the bioavailability of the GMDP compound has only been evaluated over a short time period (6 h) and the microemulsion stability over time hasn't been assessed. Surprisingly, the inventors have discovered that the addition of oligosaccharides to these formulations affects the droplet size of the emulsion, which in turn impacts the emulsion stability and thus prevent proper administration of the oligosaccharide. To circumvent this problem, the inventors have added particular stabilizing agents to emulsions according to the present invention. Said emulsions are particularly highly stable over time, meaning the particle size distribution of those emulsions does not increase for up to three months after a storage in glass bottles closed with a polyethylene top at 40° C. with 75% humidity.

To summarize, the inventors have surprisingly found that what is important for increasing the enteric absorbability is to use a formulation which is highly digestible and highly stable over time. Therefore, the ingredients of the formulation and their amount must be particularly chosen in order to obtain a formulation of the synthetic oligosaccharide which is highly digestible and highly stable over time. In addition, the present formulations are suitable for an industrial scale production.

As a consequence, the present invention concerns a pharmaceutical formulation intended for oral administration containing a synthetic oligosaccharide containing one to 18 monosaccharide units and having a therapeutical activity or a pharmaceutically acceptable additions salt or solvate thereof wherein the formulation contains:

a) the synthetic oligosaccharide (A) in an amount of up to 5% by weight of the total weight of the formulation, advantageously up to 1% by weight of the total weight of the formulation, b) a lipophilic phase (B) consisting of triglyceride of fatty acids in an amount of 50 to 80% by weight of the total weight of the formulation, advantageously of 50 to 70% by weight of the total weight of the formulation, c) at least one lipophilic surfactant (C) with HLB below 7 consisting of partial esters of polyol and fatty acids in an amount of 10 to 30% by weight of the total weight of the formulation, advantageously of 15 to 30% by weight of the total weight of the formulation, d) at least one hydrophilic surfactant (D) with HLB above 7 in an amount of up to 20% by weight of the total weight of the formulation, advantageously up to 15% by weight of the total weight of the formulation, e) optionally, at least one hydrophilic solvent (E) in an amount of up to 15% by weight of the total weight of the formulation, advantageously up to 10% by weight of the total weight of the formulation, f) between 0 and 30% by weight of the total weight of the formulation of a chemical and/or physical stabilization agent (F), advantageously between 0 and 20% by weight of the total weight of the formulation, wherein when the formulation is in a form of a reverse emulsion or microemulsion and contains at least one hydrophilic solvent (E), the physical stabilization agent is present and is silicon dioxide.

In the sense of the present invention, "a synthetic oligosaccharide containing one to 18 monosaccharide units" is intended to mean any oligosaccharide or oligosaccharide derivative that is not naturally occurring and that contains from one to 18 monosaccharide units, connected together through a covalent bond.

The synthetic oligosaccharide according to the present invention is thus not limited to "conventional" oligosaccharides (saccharides with one to 10 monosaccharide units), but comprises as well polysaccharides (saccharides with at least 10 monosaccharide units) having up to 18 monosaccharide units. Advantageously the synthetic oligosaccharide according to the present invention contains 3 to 18 monosaccharide units, more advantageously 3 to 10 units, yet even more advantageously 3 to 5 units.

In particular the covalent bond connecting the monosaccharide units is a glycosidic bond. It can also be a linker in order to form oligosaccharide dimers. Suitable monosaccharides units for use in the invention include both naturally occurring and synthetic monosaccharides on the condition that the oligosaccharide obtained is a synthetic one. In particular, the monosaccharide unit according to the present invention contains at least 5 carbon atoms. More particularly, it contains at most 9 carbon atoms. Such monosaccharide unit includes pentoses such as ribose, arabinose, xylose, lyxose and their deoxy and deoxyaminoderivatives; hexoses, such as allose, altrose, glucose, mannose, gulose, idose, galactose, talose; ketoses such as fructose and sorbose and their deoxy and deoxyaminoderivatives. In a particularly advantageous embodiment, the monosaccharide unit is a hexose.

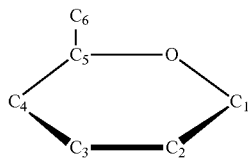

A monosaccharide unit may be linked through its $C_1$ carbon atom, also known as the anomeric carbon, to the $C_1$, $C_2$, $C_3$, $C_4$, $C_5$ and $C_6$ position (shown above) of another monosaccharide unit to form a glycosidic bond and an oligosaccharide according to the invention. In a particular embodiment, the anomeric carbon of the monosaccharide unit is attached to the $C_4$ position of another monosaccharide unit through an oxygen atom. Oligosaccharides that can be used in the present invention include: disaccharides, trisaccharides, tetrasaccharides, pentasaccharides, hexasaccharides, heptasaccharides, octasaccharides, nonasaccharides, decasaccharides, undecasaccharides and dodecasaccharides.

Advantageously, oligosaccharides according to the present invention include trisaccharides, tetrasaccharides, pentasaccharides, hexasaccharides, heptasaccharides, octasaccharides, nonasaccharides, and decasaccharides. Even more advantageously, oligosaccharides according to the present invention include pentasaccharides.

Stereoisomers of a saccharide may differ only by the configuration of the anomeric carbon, giving rise to alpha and beta anomers. By way of example, α-D-glucopyranose and β-D-glucopyranose, the two cyclic forms of glucose are shown below. For L-saccharides the alpha and beta anomers are contrariwise.

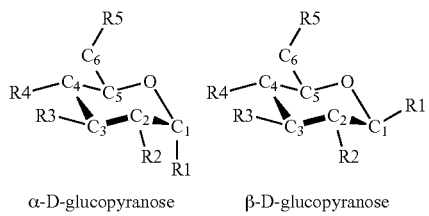

α-D-glucopyranose     β-D-glucopyranose

Monosaccharide unit rings according to the present invention can exist in an open or in a closed form, while closed forms are shown herein, open forms are also encompassed by the invention. Similarly tautomers, conformers, enantiomers, for example, are also encompassed.

"Oligosaccharide derivative" means an oligosaccharide where some of the naturally occurring functional group (hydroxyl groups, amino groups, carboxylate groups etc.) have been replaced by, or carry, a non natural substituent.

For instance, a hydroxyl group can be replaced by a hydrogen atom to yield a deoxy sugar. It can be substituted to form an ester or an ether. In a more sophisticated version it can be substituted by a pharmacologically active appendage like a receptor antagonist or an enzyme inhibitor (as indicated below). Advantageously, a non natural substituent according to the present invention does not include deoxycholic acid (DOCA).

The counter-ions, which compensate the charged forms of the compounds of the present invention, are pharmaceutically acceptable counter-ions such as hydrogen, or typically alkali or alkali-earth metals ions, which include sodium, calcium, magnesium and potassium. Salts of pharmaceutically acceptable organic compounds, particularly amine derived salts, are also encompassed. A list of the pharmaceutically acceptable salts can be found in J. Pharm. Sci., 66, 1977, 1-19 or in Int. J. Pharm., 33, 1986, 201-217.

The oligosaccharides according to the present invention can be conjugated to a small molecule drug, like a receptor antagonist such as described in WO 2007/042 470, or like an enzyme inhibitor such as described in WO01/42262, they can also be conjugated to biotin or to a biotin derivative, in particular by using a linker such as described in EP 1 322 673, or in WO 2006/067 173, or in WO 2007/042 469.

The oligosaccharide according to the present invention display pharmacological activities allowing their use as therapeutic agents. For example, they can be used in the prevention and the treatment of venous thromboembolism (phlebitis, deep veins thrombosis, pulmonary embolism) and/or a condition related to blood coagulation disorders. They can also be used in the prevention and the prevention and the treatment of arterial thrombosis (acute coronary syndrome, myocardial infarction, stroke).

In particular the oligosaccharide according to the present invention is a heparin-related oligosaccharide, more particularly a heparin-related pentasaccharide. Advantageously, the oligosaccharide according to the present invention is chosen between:

Fondaparinux, in particular the sodium salt of fondaparinux of the following formula:

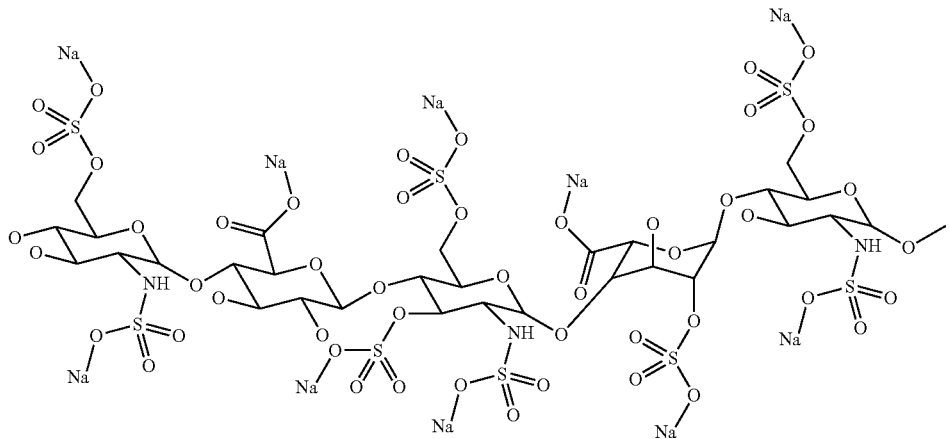

(Molecular Formula: C31H43N3Na10O49S8; Molecular Weight: 1728.0891) and the benzathine salt of fondaparinux where the above sodium ions are replaced by protonated benzathine of formula $C_6H_5CH_2NHCH_2CH_2NHCH_2C_6H_5$ herein below refers to Fondaparinux Benzathine
and the oligosaccharides described in U.S. Pat. No. 4,818,816 compound 675, in particular in the form of its sodium salt, of the following formula:

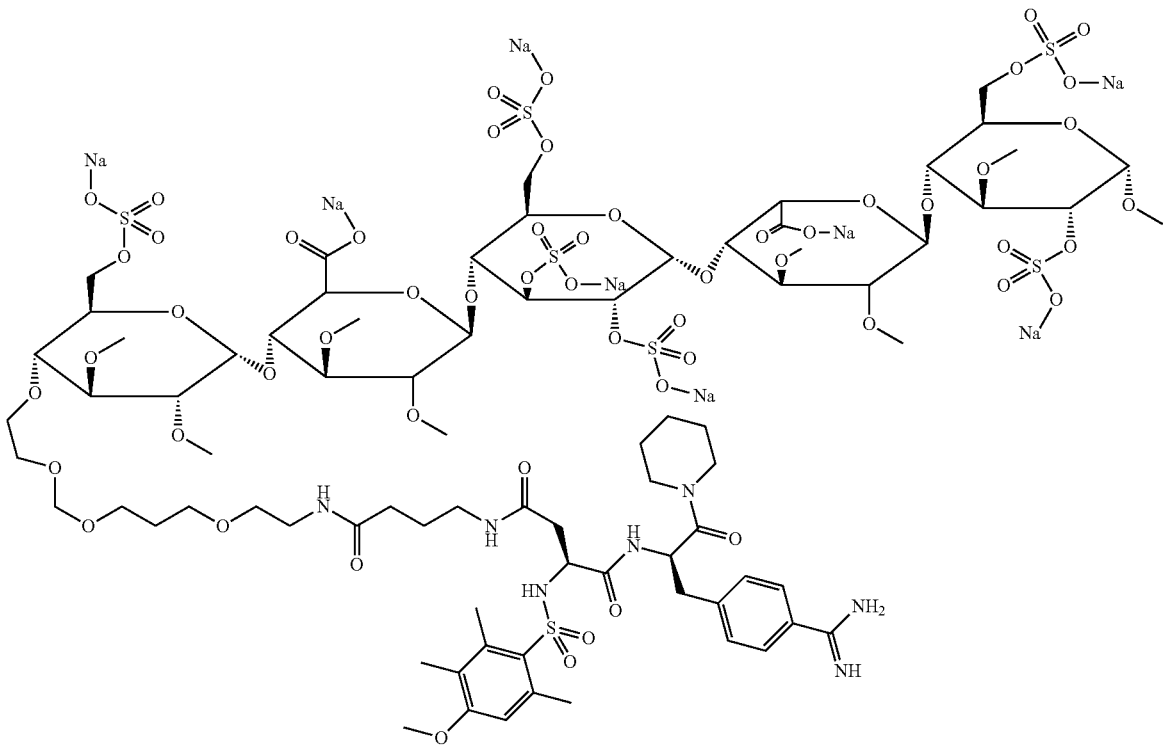

(Molecular Weight: 2469.19; Molecular Formula: C79H117N7Na8O56S7) and the oligosaccharides described in WO01/42262;
compound 609, in particular in the form of its sodium salt, of the following formula:
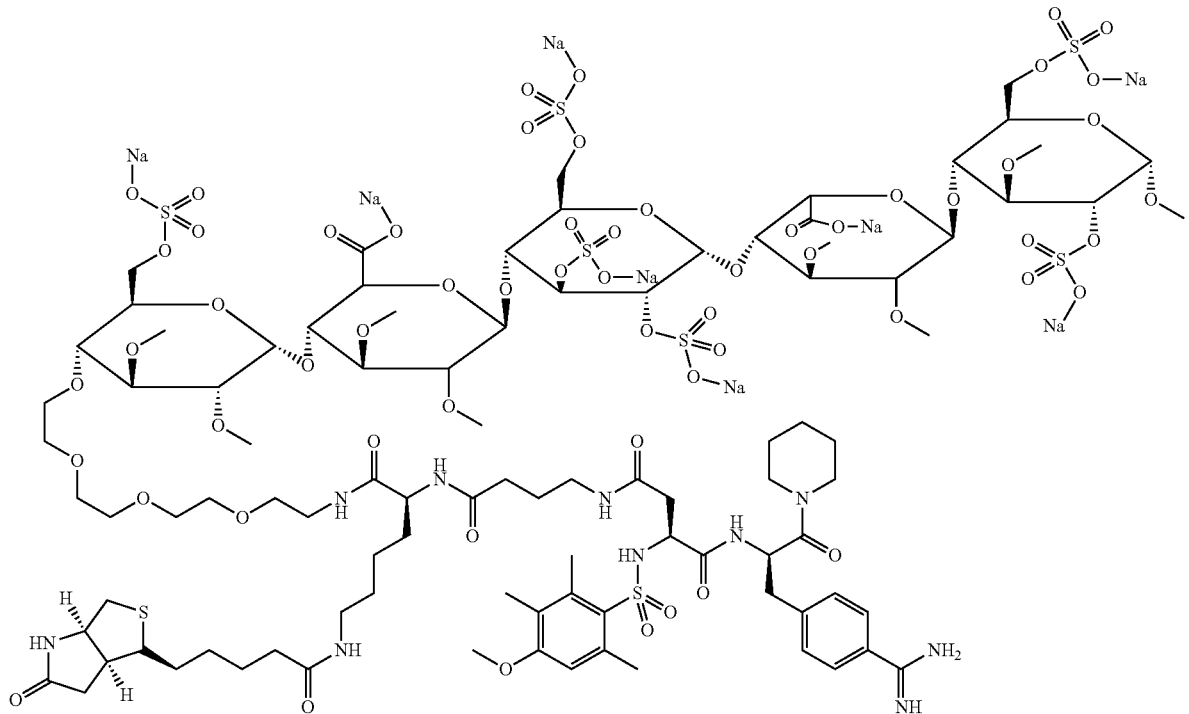
(Molecular Weight: 2823.67, Molecular Formula: C95H143N11Na8O59S8) and the oligosaccharides described in WO 2006/067173
compound 122, in particular in the form of its sodium salt, of the following formula:
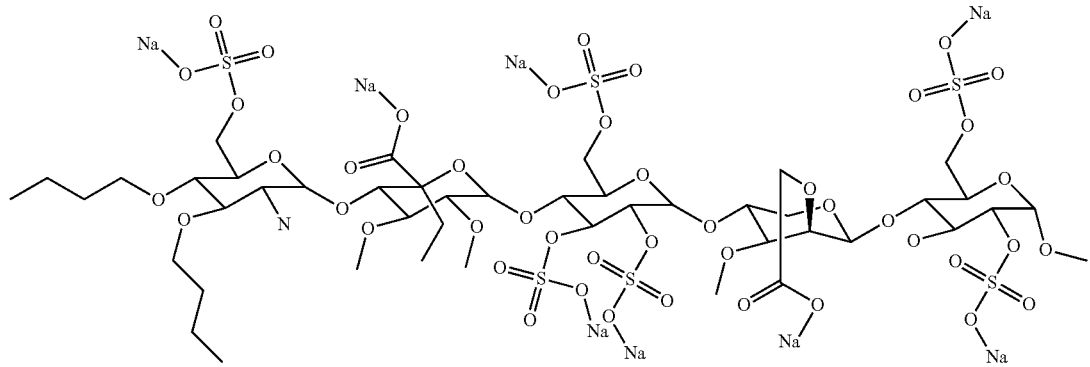

(Molecular Weight: 1734.36; Molecular Formula: C46H71NNa8O45S6) and its biotinylated counterpart, of the following formula:
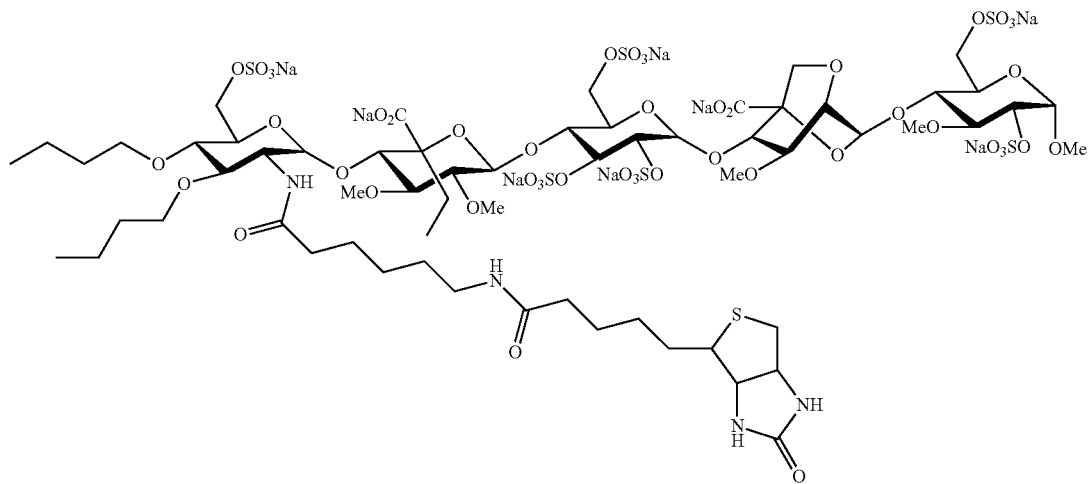
and compound 147, in particular in the form of its sodium salt, of the following formula:
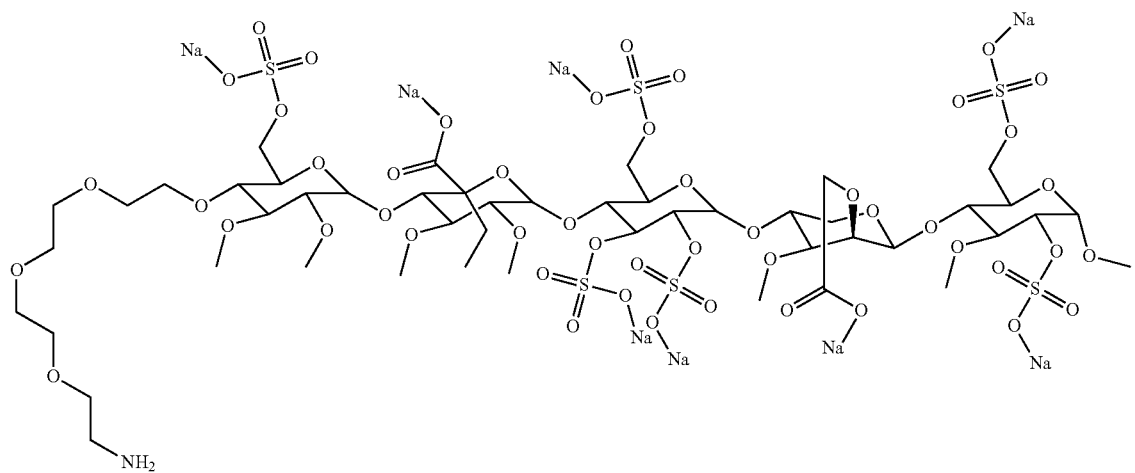

(Molecular Weight: 1826.41; Molecular Formula: C48H75NNa8O49S6) and its biotinylated counterpart, of the following formula:

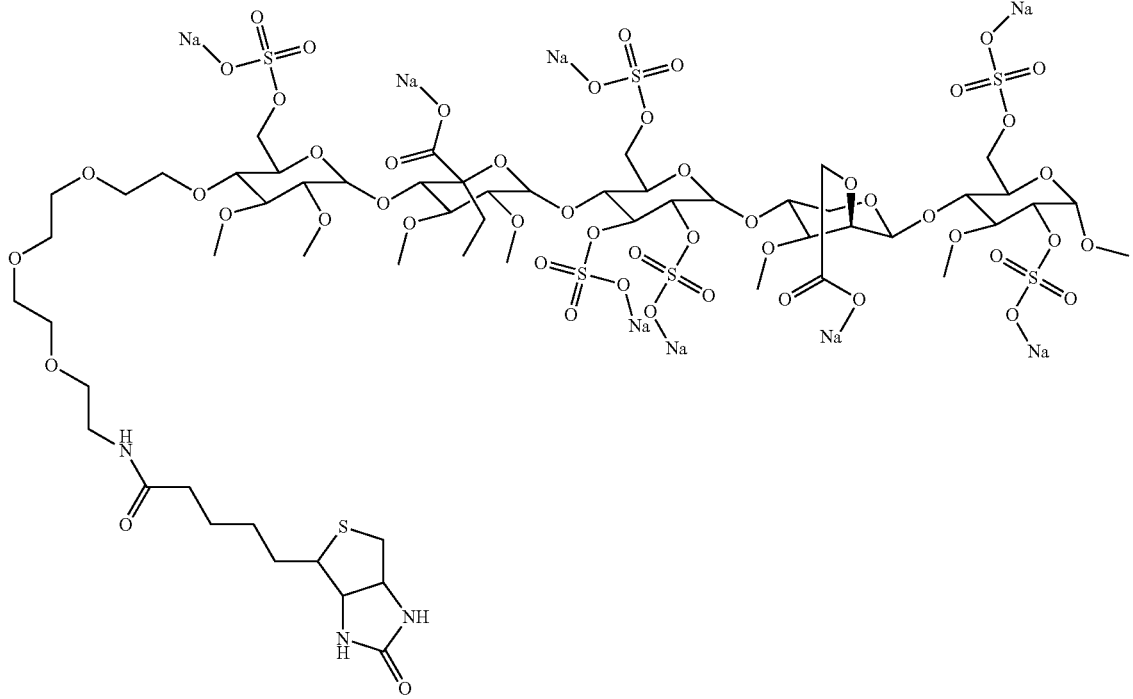

and the oligosaccharides described in WO/2008/041131.

It will be appreciated that ionisable groups may exist in the neutral form shown in formulae herein above, or may exist in charged form e.g. depending on pH. Thus, a carboxylate group may be shown as COOH, which is merely representative of the neutral carboxylate group. The present invention also encompasses other charged forms (i.e. COO).

Similarly, references herein to cationic and anionic groups should be taken to refer to the charge that is present on that group under physiological conditions e.g. where a sulphate group O—$SO_3H$ is deprotonated to give the anionic O—$SO_3^-$ group, this deprotonation is one that occurs at physiological pH. In addition where a carboxyl group COOH is deprotonated to give the anionic $COO^-$ group, this deprotonation is one that can occur at physiological pH. Moreover, charged salts of the molecules of the invention are encompassed.

In particular the synthetic oligosaccharide is in the form of its sodium salt.

The synthetic oligosaccharide (A) according to the present invention is present in the formulation according to the present invention in an amount which is not more than 5% by weight of the total weight of the formulation, advantageously not more than 1% by weight of the total weight of the formulation. In particular the synthetic oligosaccharide is present in the formulation of the present invention in an amount of at least 0.1% by weight of the total weight of the formulation, more preferably at least 0.5%, more particularly when the oligosaccharide is a heparin-related pentasaccharide.

The formulation according to the present invention contains a lipophilic phase (B) which consists in triglycerides of fatty acids in an amount of 50 to 80% by weight of the total weight of the formulation, advantageously of 50 to 70% by weight of the total weight of the formulation, more advantageously of 55% to 65% by weight of the total weight of the formulation, still more advantageously of 58 to 64% by weight of the total weight of the formulation. The presence of a minimum of 50% by weight of the total weight of the formulation of triglycerides is necessary in order for the formulation to be digestible. This means that glycerides are being deesterified in 2-monoglycerides and free fatty acids by pancreatic lipase in the GI juices.

The formulation can not contain more than 80% by weight of triglycerides, since the synthetic oligosaccharide according to the present invention is not readily soluble in the triglycerides and other ingredients have to be included in the formulation in order to obtain a formulation of the synthetic oligosaccharide. In the sense of the present invention the term "triglycerides of fatty acids" is intended to mean any triglycerides of saturated or unsaturated fatty acid which are pharmaceutically and orally acceptable. In particular they have the following formula:

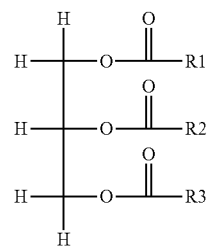

in which R1, R2 and R3 represent independently of each other the alkyl or alkenyl group of the parent fatty acid.

The fatty acid can be saturated or unsaturated. In particular the fatty acid is saturated since unsaturated fatty acid gives slower digestion kinetic and lower digestion percentages.

The most common saturated fatty acids are indicated in the following table 1:

TABLE 1

| Common name | IUPAC name | Chemical structure | Abbr. | Melting point (° C.) |
|---|---|---|---|---|
| Butyric | Butanoic acid | $CH_3(CH_2)_2COOH$ | C4:0 | −8 |
| Caproic | Hexanoic acid | $CH_3(CH_2)_4COOH$ | C6:0 | −3 |
| Caprylic | Octanoic acid | $CH_3(CH_2)_6COOH$ | C8:0 | 16-17 |
| Capric | Decanoic acid | $CH_3(CH_2)_8COOH$ | C10:0 | 31 |
| Lauric | Dodecanoic acid | $CH_3(CH_2)_{10}COOH$ | C12:0 | 44-46 |
| Mystiric | Tetradecanoic acid | $CH_3(CH_2)_{12}COOH$ | C14:0 | 58.8 |
| Palmitic | Hexadecanoic acid | $CH_3(CH_2)_{14}COOH$ | C16:0 | 63-64 |
| Stearic | Octadecanoic acid | $CH_3(CH_2)_{16}COOH$ | C18:0 | 69.9 |
| Arachidic | Eicosanoic acid | $CH_3(CH_2)_{18}COOH$ | C20:0 | 75.5 |
| Behenic | Docosanoic acid | $CH_3(CH_2)_{20}COOH$ | C22:0 | 74-78 |
| Lignoceric | Tetracosanoic acid | $CH_3(CH_2)_{22}COOH$ | C24:0 | |

Therefore, advantageously R1, R2 and R3 represent a straight or branched chain, in particular straight, $C_3$-$C_{23}$ alkyl or alkenyl group, more advantageously alkyl group, in particular a $C_5$-$C_{13}$ alkyl or alkenyl group, advantageously alkyl group, still more advantageously a $C_7$-$C_9$ alkyl or alkenyl group, in particular alkyl group. In particular, fatty acids are saturated fatty acids and are medium chain fatty acids. Therefore, the lipophilic phase (B) consists of triglycerides of long, (such as for example soya bean oil and fish oil), medium or short (such as for example glyceryl triacetate) chain fatty acids, in particular of triglycerides of medium chain fatty acids, more particularly of triglycerides of caprylic acid, capric acid or mixture thereof (such as for example the commercial product Mygliol 812®, Captex 355®, Estasan®, Neobee M5® and Labrafac CC®, in particular Mygliol 812®), still more particularly of capric acid (such as for example the commercial product Captex 1000®).

Among all the triglycerides, triglycerides of medium chain fatty acid (i.e. $C_6$-$C_{12}$ fatty acids) are the most digestible ones, and in particular triglycerides of caprylic acid and/or capric acid, more particularly triglycerides of capric acid. However, surprisingly the inventors have found that $C_8$-$C_{10}$ fatty acids have a better biodisponibility. Therefore, the triglycerides of $C_8$-$C_{10}$ fatty acids are the most advantageous one in the formulation according to the present invention.

The formulation according to the present invention contains at least one (or in an advantageous manner a mixture of) lipophilic surfactant (C) with HLB value below 7 consisting of partial esters of polyol and fatty acids in an amount of 10 to 30% by weight of the total weight of the formulation, advantageously of 15 to 30% by weight of the total weight of the formulation, still more advantageously of 15 to 27% by weight of the total weight of the formulation, even still more advantageously of 16 to 26% by weight of the total weight of the formulation.

The HLB value (hydrophilic-lipophilic balance) is an empirical parameter commonly used by the one skilled in the art to characterize the relative hydrophilicity and hydrophobicity of a non ionic surfactant. Surfactants with a HLB value below 7 are more hydrophobic and have greater solubility in oils, whereas surfactants with a HLB value above 7 are more hydrophilic and have greater solubility in aqueous mediums. Methods well known by the one skilled in the art are used in order to determine the HLB value of a surfactant by calculating values for the different regions of the molecule.

The lipophilic (C) surfactant participates to the increase in digestibility of the synthetic oligosaccharide. Optionally it can participates to the formation of an homogenous system The minimal amount of 10% by weight of the total weight of the formulation in lipophilic surfactant (C) is necessary in order to obtain a formulation containing both the synthetic oligosaccharide (A) and the lipophilic phase (B).

Advantageously, the formulation according to the present invention does not contain more than 30% by weight of the total weight of the formulation of the lipophilic surfactant (C) according to the present invention since otherwise the formulation is less digestible.

In the sense of the present invention the term "partial esters of polyol and fatty acids" is intended to mean any partial esters obtained by esterification of polyols and saturated or unsaturated fatty acids, in particular saturated fatty acids, which are pharmaceutically and orally acceptable.

The most common saturated fatty acids are indicated in the above-mentioned table 1. Advantageously the fatty acids are medium chain fatty acids, such as $C_6$-$C_{12}$ fatty acids, in particular caprylic and/or capric acid, more particularly capric acid. The polyols can be for example chosen in the group consisting of propylene glycol and glycerol. For example the partial esters of polyol and fatty acids can be propylene glycol mono- and/or di-esters of fatty acids (such as the propylene glycol monolaurate sold under the trade name Lauroglycol®, the propylene glycol monomyristate sold under the trade name Mirpyl® or the propylene glycol dicaprylate/dicaprate sold under the trade name Captex. 200®, Miglyol 840® or Neobee M-20®) and/or polyglycerol esters of fatty acids (such as the polyglyceryl oleate sold under the trade name Plurol Oleique® or Drewpol 10.10.10® or the polyglyceryl mixed fatty acids sold under the trade name Caprol ET®).

In particular the lipophilic surfactant (C) can consists in partial esters of propylene glycol and fatty acids (such as for example the commercial product Capryol PGMC® and Capmul PG-8®). Advantageously, the lipophilic surfactant (C) consists of a mixture of mono and diglyceride of fatty acids, more advantageously a mixture of mono and diglyceride of medium chain fatty acids still more advantageously a mixture of mono and diglyceride of caprylic and/or capric acid (such as for example the commercial product Capmul MCM and Capmul MCM C8®, Imwitor 988®, Imwitor 742®), even still more particularly a mixture of mono and diglyceride of capric acid (such as for example the commercial product Capmul MCM C100 or Imwitor 308®).

The inventors have surprisingly found that among all the partial esters of polyols and fatty acids, the mixture of mono and diglyceride of medium chain saturated fatty acid (i.e. $C_6$-$C_{12}$ fatty acids) are the most digestible one, and in particular the mixture of mono and diglyceride of caprylic acid and/or capric acid, more particularly the mixture of mono and diglyceride of capric acid.

The formulation according to the present invention contains at least one (or in an advantageous manner a mixture of) hydrophilic surfactant (D) with HLB value above 7 in an amount of up to 20% by weight of the total weight of the formulation, advantageously up to 15% by weight of the total weight of the formulation, more advantageously of at least 3% by weight of the total weight of the formulation, still more advantageously of at least 5% by weight of the total weight of the formulation, even still more advantageously of at least 9% by weight of the total weight of the formulation, in particular of up to 10% by weight of the total weight of the formulation.

The presence of a hydrophilic surfactant is necessary in order to increase the solubility of the synthetic oligosaccharide in the lipophilic phase (B) according to the present invention and to improve the dispersibility of the formulation. However, the hydrophilic surfactant above a certain extent has a negative impact on the digestibility of the formulation. Therefore, its amount should not exceed 20% by weight of the total weight of the formulation.

In the sense of the present invention, the term "hydrophilic surfactant" is intended to mean any hydrophilic surfactant having a HLB value above 7 and advantageously above 10 which are pharmaceutically and orally acceptable.

Advantageously, the hydrophilic surfactant can be:
  phospholipids, in particular lecithins, e.g. soybean lecithins;
  polyoxyethylene sorbitan fatty acids derivatives, such as for example the polyoxyethylene (20) monolaurate (sold under the trade name Tween 20®), polyoxyethylene (20) monooleate (sold under the trade name Tween 80® and/or Crillet 4®) or the polyoxyethylene (20) monopalmitate (sold under the trade name Montanox 40®);
  castor oil or hydrogenated castor oil ethoxylates with a HLB value above 10, such as polyoxyethylene (35) castor oil (sold under the trade name Cremophor EL®), polyoxyethylene (40) hydrogenated castor oil (sold under the trade name Cremophor RH40®), polyoxyethylene (40) castor oil (sold under the trade name Etocas 40®) or polyoxyethylene (60) hydrogenated castor oil (sold under the trade name Nikkol HCO-60®);
  fatty acids ethoxylates with a HLB value above 10, such as polyoxyethylene (8) stearate (sold under the trade name Myrj 45®), polyoxyethylene (30) monolaurate (sold under the trade name Tagat L®), polyoxyethylene (20) stearate (sold under the trade name Marlosol 1820®) or polyoxyethylene (15) oleate (sold under the trade name Marlosol OL15®);
  alcohol ethoxylates with a HLB value above 10, such as polyoxyethylene (10) oleyl ether (sold under the trade name Brij 96®), polyoxyethylene (15) oleyl ether (sold under the trade name Volpo 015®), polyoxyethylene (30) oleyl ether (sold under the trade name Marlowet OA30®) or polyoxyethylene (20) $C_{12}$-$C_{14}$ fatty ether (sold under the trade name Marlowet IMA20®);
  polyoxyethylene-polyoxypropylene co-polymers and block co-polymers with a HLB value above 10, such as the products sold under the trade name Syperonic PE L44® with a HLB value=16 or the products sold under the trade name Syperonic F127® with a HLB value=22;
  anionic surfactants, such as the sodium lauryl sulphate, the sodium oleate or the sodium dioctylsulphosuccinate or
  alkylphenol surfactants with a HLB value above 10, such as the polyoxyethylene (9-10) nonylphenol (sold under the trade name Triton N-101®) or the polyoxyethylene (9) nonylphenol (sold under the trade name Synperonic NP9®);
  Vitamin E;
  D-alpha-tocopheryl Polyethyelene glycol Succinate (TPGS) or
  PEG 15 Hydroxystearate (sold under the trade name Solutol HS15®).

Advantageously the hydrophilic surfactant is a polyethoxylated surfactant, more advantageously it is chosen in the group consisting of polyoxyethylene sorbitan fatty acid esters, polyoxyethylene alkyl ethers and polyoxyethylene esters of fatty acids such as polyoxyethylene esters of glycerol and fatty acids.

Advantageously the fatty acids are saturated or unsaturated. The most common saturated fatty acids are indicated in the above-mentioned table 1. Advantageously the fatty acids are medium chain fatty acids, such as $C_6$-$C_{12}$ fatty acids, in particular lauric, caprylic and/or capric acid.

Advantageously, the number of ethylene oxide groups units in the surfactant is chosen between 4 and 20. Advantageously the hydrophilic surfactant (D) is chosen in the group consisting of polyoxyethylene (20) monooleate (such as for example the commercial product Tween 80®), PEG 8 caprylic/capric glycerides (such as for example the commercial product Labrasol®), PEG 6 caprylic/capric glycerides (such as for example the commercial product Softigen 767®), poly(oxyethylene)(4)Lauryl ether (such as for example the commercial product Brij 30®) and mixtures thereof.

The formulation according to the present invention can optionally contain at least one (or in an advantageous manner a mixture of) hydrophilic solvent (E) in an amount of up to 15% by weight of the total weight of the formulation, advantageously up to 10% by weight of the total weight of the formulation. When the hydrophilic solvent is present in the formulation according to the present invention, its minimal content is advantageously of 1% by weight of the total weight of the formulation, still more advantageously of 1.5% by weight of the total weight of the formulation.

The hydrophilic solvent allows the solubilization of the synthetic oligosaccharide, if such oligosaccharide is particularly hydrosoluble and/or is not soluble in the mixture of (B), (C) and (D).

In the sense of the present invention, the term "hydrophilic solvent" is intended to mean any solvent which allow the solubilization of the synthetic oligosaccharide according to the present invention. In particular, it is chosen in the group consisting of propylene glycol, PEG 400, diethylene glycol monoethyl ether, glycerol triacetate, ethanol, glycerol, dimethylisosorbide, N-methyl-2-pyrrolidone, poloxamers, water and mixtures thereof, advantageously in the group consisting of propylene glycol, PEG 400, ethanol, water and mixtures thereof.

The formulation according to the present invention can contain between 0 and 30%, advantageously between 0 and 20%, by weight of the total weight of the formulation of a chemical and/or physical stabilization agent (F).

In particular, when the formulation is in a form of a reverse emulsion or microemulsion and contains at least one hydrophilic solvent (E), the physical stabilization agent is present and is silicon dioxide.

In the sense of the present invention, the term "chemical and/or physical stabilization agent" is intended to mean any pharmaceutical ingredient which will improve the oligosaccharide chemical stability in the formulation in order to comply with the ICH Harmonized Tripartite Guideline ICH Q3B (Impurities In new drug products) requirements Current step 4 version dated Jun. 2, 2006 and which will improve the oligosaccharide formulation physical stability in order to obtain an homogeneous formulation.

In particular in the case where the formulation contains the hydrophilic solvent (E) and the formulation is in the form of a reverse emulsion or microemulsion, the chemical stabilization agent can be a lipophilic surfactant: such as
  acetic, succinic, lactic, citric and/or tartaric esters of mono- and/or di-glycerides of fatty acids such as distilled acetylated monoglycerides (sold under the trade name Myvacet 9-45®), caprylic/capric diglyceryl succinate (sold under the trade name Miglyol 829®), mono/di-succinylated monoglycerides (sold under the trade name Myverol SMG®), glyceryl stearate citrate (sold under the trade name Imwitor 370®), glyceryl monostearate/citrate/lactate (sold under the trade name Imwitor 375®)

or diacetyl tartaric asters of monoglycerides (sold under the trade name Cordatem T22®);

acid ester ethoxylates formed by reacting ethylene oxide with fatty acids or glycerol esters of fatty acids with a HLB value below 10, such as polyoxyethylene (4) lauric acid (sold under the trade name Crodet 04®), polyoxyethylene (2) stearic acid (sold under the trade name Cithrol 2MS®), polyoxyethylene (3) stearic acid (sold under the trade name Marlosol 183®) or glyceryl 12 EO dioleate (sold under the trade name Marlowet G12DO®);

sorbitan esters of fatty acids, such as sorbitan monolaurate (sold under the trade name Span 20® or Crill 1®) or sorbitan mono-oleate (sold under the trade name Crill 4®), transesterification products of natural or hydrogenated vegetable oil triglyceride and polyalkylene polyol with a HLB value below 10 such as polyoxyethylated apricot kernal oil (sold under the trade name Labrafil M1944CS®), polyoxyethylated corn oil (sold under the trade name Labrafil M2125CS®) or polyoxyethylated hydrogenated oil (sold under the trade name Gelucire 37/06®) or Alcohol ethyoxylates with a HLB value below 10 such as polyoxyethylated (3) oleyl ether (sold under the trade name Volpo N3®), polyoxyethylated (2) oleyl ether (sold under the trade name Brij 93®) or polyoxyethylated (4) lauryl ether (sold under the trade name Marlowet LA4®).

In particular in the case where the formulation contains the hydrophilic solvent (E) and the formulation is in the form of a reverse emulsion or microemulsion, the physical stabilization agent can be a solid substrate such as silicon dioxide (sold under the trade name Aerosil A300® or R972®).

The chemical stabilization agent can be:

Buffering agents to stabilize the oligosaccharide and reverse emulsion (such as citrate, phosphate or acetate buffers) and/or Thickening agents to stabilize the reverse emulsion stability such as partially hydrogenated oils, hydrogenated oils, monoesters of unsaturated or saturated fatty acids.

In a particular embodiment, the formulation according to the present invention is liquid and in particular has the form of a solution.

In another particular embodiment, in the case where the hydrophilic solvent (E) is present, the formulation according to the present invention is in the form of a reverse microemulsion (e.g. water-in-oil) or a reverse emulsion (e.g. water-in-oil) or a micellar solution in oil. In this case the synthetic oligosaccharide is present in the hydrophilic phase of the microemulsion or of the emulsion or in the micelles of the micellar solution. Any stabilization agents (F) needed to stabilize the reverse emulsion could be added. This includes without limitations thickening agents, polymers, particles generating steric hindrance at the interface (silicon dioxide . . . ) as indicated above.

In the particular case in which the physical agent is silicon dioxide, said silicon dioxide is advantageously present in an amount of 5-20% by weight of the total weight of the formulation, more advantageously in an amount of 6-18%, still more advantageously in an amount of 7-16%, 8-14% or 9-12%.

The silicon dioxide according to the present formulation is a colloidal silicon dioxide. Colloidal silicon dioxide is also known as fumed silicon dioxide, silica fume or pyrogenic silica. Such silicon dioxides are commercially available under the trademarks Aerosil® (Evonik industries), Cab-O-Sil® (Cabot Corporation) and Wacker HDK® (Waccker-Chemie GmbH).

Silicon dioxides according to the present formulation can be hydrophilic or hydrophobic. Hydrophilic silicon dioxides can be typically produced by hydrolysing chlorosilanes at 1800° C., using a hydrogen-oxygen flame. Immediately after cooling, hydrophilic silicon dioxides can be further treated in a fluid bed reactor with organosilicon compounds in order to produce hydrophobic silicon dioxides. Those organosilicon compounds include, without limitation, D4 (octamethylcyclotetrasiloxane), DDS (dimethyldichlorosilane), DMPS (polydimethylsiloxane), HMDS (hexamethyldisilazane), HMDS and AS (hexamethyldisilazane et aminosilane), methacrylsilane, octylsilane, and hexadecylsilane. The carbon content in the hydrophobic silicon dioxide is preferably in an amount between 0.5 and 6.5% by weight of the total weight of said silicon dioxide. Advantageously, the carbon content is in an amount between 0.5 and 5.5%, 0.5 and 4.5%, 0.5 and 3.5%, 0.5 and 2.5%, 0.5 and 1.5% of the total weight of said silicon dioxide. More preferably, the carbon content in the hydrophobic silicon dioxide is in an amount between 0.5 and 1.5% of the total weight of said silicon dioxide.

Through hydrophobic treatment, the density of silanol groups per $nm^2$ decreases from approximately 2 $SiOH/nm^2$ for hydrophilic silicon dioxides to 0.75 $SiOH/nm^2$ for the hydrophobic ones.

The silicon dioxide according to the present formulation is preferably hydrophobic, and more preferably hydrophobic after a treatment with DDS (dimethyldichlorosilane). Advantageously, the silanol groups density of the hydrophobic silicon dioxide according to the present invention is of 0.75 $SiOH/nm^2$. In particular, the hydrophobic silicon dioxide according to the present invention is commercially available under the name Aerosil R972®, and more particularly under the name Aerosil R972®Pharma.

The average primary particle size of the silicon dioxide according to the present formulation can be comprised between 7 and 40 nm, advantageously between 7 and 20 nm, more advantageously between 7 and 10, 10 and 13, 13 and 16, or 16 and 20.

The specific surface area of the silicon dioxide according to the present formulation can be comprised between 50 and 450 $m^2/g$, when measured according to the BET method. Advantageously, said specific area is comprised between 90 and 450 $m^2/g$, advantageously between 90 and 400 $m^2/g$, 90 and 350 $m^2/g$, 90 and 300 $m^2/g$, or 90 and 250 $m^2/g$, 90 and 200 $m^2/g$, and even more advantageously between 90 and 150 $m^2/g$.

The tapped density of the silicon dioxide according to the present formulation can be comprised between 0.04 and 0.28 $g/cm^3$ (DIN EN ISO 787/11, August 1983). Advantageously, said density is about 0.04 $g/cm^3$, 0.05 $g/cm^3$, 0.06 $g/cm^3$, 0.07 $g/cm^3$, 0.08 $g/cm^3$, 0.09 $g/cm^3$, 0.1 $g/cm^3$ and 0.2 $g/cm^3$. More advantageously, said density is about 0.05 $g/cm^3$.

In the particular case in which the physical agent is silicon dioxide and the hydrophilic solvent (E) is present, the role of the silicon dioxide is to stabilize the formulation and decrease the bioavailability variability of the oligosaccharide (A), particularly when said formulation is administered in dogs.

Advantageously the formulation according to the present invention is homogenous. In particular, the formulation could be a homogeneous formulation consisting of a reverse microemulsion, reverse emulsion or micellar solution in which the oligosaccharide is included in the hydrophilic phase.

In the sense of the present invention, an "homogeneous pharmaceutical formulation" is intended to mean any single or multiple phase formulation which can be used in the manufacture of a bulk fill formulation in compliance with FDA Guidance for Industry ANDAS: Blend Uniformity dated Aug. 3, 1999, and/or in the manufacture of a viable final pharmaceutical dosage form in compliance with the Content Uniformity Test criteria (excluding mass variation evaluation—European Pharmacopeia Uniformity of Dosage Units 2.9.40, USP General Chapter <905> and Japanese Pharmacopeia 6.02 Uniformity of Dosage units) and/or which can meet the compliance of stable drug substance assay results on stratified samples taken across the manufacturing process.

The formulation according to the present invention can be prepared according to the following process:

First, in step 1, the synthetic oligosaccharide (A) is mixed with the hydrophilic solvent (E) until complete dissolution. Optionally, the hydrophilic surfactant (D) and/or hydrophobic surfactant (B) could be added. The dissolution duration is established until complete dissolution is achieved by the mean of a process control by visual and microscopic observations performed at time intervals dependent upon batch size. The mixing speed is dependent upon the batch size and shape of the equipment. The process is performed at room temperature or 5° C. above the melting point of the highest melting point ingredient. The dissolution kinetic can be improved by temperature increase. Typically, dissolution of oligosaccharides can be achieved in the hydrophilic phase at room temperature within 5 to 15 minutes using standard low shear mixer.

In a step 2, the lipophilic phase (B), rest of the components and the previous oligosaccharide solution obtained in step 1 are mixed to obtain the formulation according to the present invention. In the case of a reverse emulsion, microemulsion stabilizing agents (F) might be preliminary added or added consecutively.

In case where the hydrophilic solvent (E) is present, the mixing of step 2 with the lipophilic phase can be carried out with or without applying high shear mixing by method well known by the one skilled in the art in order to obtain a reverse emulsion water in oil, a reverse microemulsion water in oil or a micellar solution in oil.

The formulation according to the present invention is digestible. This means glycerides are being deesterified in 2-monoglycerides and free fatty acids by pancreatic lipase in the GI (Gastro-Intestinal) juices. Pancreatic lipase in the presence of colipase catalyses the lipolysis (also termed hydrolysis or de esterification) of emulsified oils, is a process that results in the production of fatty acids. The rate of fatty acid generation, and thus a measure of the rate of lipolysis can be followed via continuous titration with a pH-stat as described in example 2. Advantageously, the extent of digestion after 60 min in a pancreatin solution containing a pancreatin extract having an activity of approximately 8 Tributyrin Units (TBUs) per milligram of dry powder in distilled water at the dosage of 250 mg/ml at 37.5° C.+/−0.5° C. (according to the test indicated in example 2) (and thus rate of digestion) is such that at least 1 mmol of the total free fatty acid is released/g of the formulation according to the present invention, more advantageously at least 1.5 mmol of the total free fatty acid is released/g of the formulation according to the present invention, still more advantageously at least 1.7 mmol of the total free fatty acid is released/g of the formulation according to the present invention.

In another advantageous embodiment, the extent of digestion after 60 min in CPS models (and thus rate of digestion) is such that at least 0.4 mmol of the $C_{10}$ free fatty acid (i.e. capric acid) is released/g of the formulation according to the present invention, more advantageously at least 0.6 mmol of the $C_{10}$ free fatty acid is released/g of the formulation according to the present invention, still more advantageously at least 0.7 mmol of the $C_{10}$ free fatty acid is released/g of the formulation according to the present invention.

The formulation according to the present invention is liquid or semi-solid (i.e. present a melting temperature range above room temperature) and can be orally administered to a patient in need thereof using pharmaceutical dosage form well known by the one skilled in the art. In particular such pharmaceutical dosage form can be hardshell capsule or softgel capsule. Such capsules include hard gelatine capsules and soft gelatine capsules. This formulation can also be translated into a conventional solid dosage form by the means of techniques well known by the one skilled in the art such as adsorption, hot melt granulation/coating and/or by the mean of selected carriers, diluents, additives and/or binders.

The site of absorption of the synthetic oligosaccharide is in the intestine. Therefore, it is advantageous to co-deliver the formulation (containing (B), (C), (D) and optionally (E) and (F)) and the synthetic oligosaccharide to its site of absorption and where the formulation is digested. In this case, dilution of the formulation in the stomach should be avoided. As a consequence, in a particular embodiment of the pharmaceutical dosage form is an enteric dosage form which contains the formulation according to the present invention.

Various drug delivery systems can be envisaged by the one skilled in the art in order to obtain an enteric dosage form. Various materials enable to obtain an enteric effect. These materials can be used to obtain matrix forms (such as described in CA2439366) or coated forms. The best enteric and protective results are being obtained using coated dosage forms.

The various type of material which can be used to manufacture an enteric dosage form are as follow:
  Polymers sensitive to intestinal enzymes such as esterase and lipase (for example Salol, shellac, lipidic compounds (stearic acid, partial glycerides), carnauba wax, hydrogenated castor oil) or protease (for example keratine, gluten, zein)
  Polymers soluble in intestinal pH
This option is the most widely used in the pharmaceutical industry. These polymers can be:
  cellulosic and starch derivatives. For example cellulose acetophtalate, hydroxypropyl methylcellulose, cellulose acetohemisuccinate, starch and amylose acetophtalate.
  Vinylic derivatives. For example polyvinyl acetate, polyvinyl acetophtalate.
  Acrylic derivatives. For example Eudragit L.
  Maleic acid copolymers.

Advantageously the enteric pharmaceutical dosage form is pH dependent and therefore is using polymers soluble in intestinal pH. Advantageously, the enteric pharmaceutical dosage form is an enteric coated capsule, in particular an enteric coated soft gelatin capsule, more particularly an enteric coated oval soft gelatin capsule, still more particularly an enteric coated 7.5 oval soft gelatin capsule. Advantageously the gelatin capsule has a hardness of between 8 to 12 N according to the test indicated below, in particular of 9.5N.

The manufacture of an enteric coated 7.5 oval soft gelatin capsule formulation is well known by the one skilled in the art and can be as follow:

Soft Gelatine Capsule Manufacture
Gelatin Preparation

The required quantities of glycerol and purified water are added to the gelatine melter and heated while mixing. The required quantity of gelatine is added and the mixing is continued under heat and vacuums to melt, blend, and deaerate the molten gelatine. The molten gelatine is checked for clarity, then transferred to a heated storage vessel. The molten gelatine is maintained at 50-65° C. prior to and during encapsulation. The required quantities of the opacifier and colouring agents are added to the molten gelatine and mixed until the opaque colour is uniform. The colour is then checked. The shell formulation applied for 7.5 oval capsule manufacture is gelatine/glycerol/purified water (43.85/22.02/34.13).

Encapsulation

Soft gelatine capsules are prepared by the rotary die process. The heated gelatine is fed to the encapsulation machine where it enters two spreader boxes, which cast the gelatine on a cooling drum, thus forming two gelatine ribbons. Each gelatine ribbon is lubricated with medium chain triglycerides (MCT) on the internal side and with MCT containing 0.3% w/w lecithin on the external side. The MCT prevents the gelatine from sticking to the equipment. The lecithin prevents the capsules from sticking together after manufacture, prior to drying. The ribbons are then conveyed to the encapsulation rollers. Die cavities (7.5 oval in this case) designed to form the capsules are located on the circumference of the two adjacent rollers that rotate and press the gelatine ribbons between them. The fill solution (in this case the formulation according to the present invention) is injected between the gelatine ribbons forcing them to expand and fill the die cavities. As the capsules are filled, they are simultaneously shaped, sealed and cut from the gelatine ribbon by the encapsulation rollers. Capsule fill, shell weight, and seal thickness, tests are performed.

Drying

Filled capsules are transferred to rotating drying baskets. The capsules are tumbled in each basket to remove sufficient moisture for improved handling. The capsules are then transferred onto trays, the trays are stacked, and the stacks are placed in drying tunnels. A hardness test is performed to determine when and the capsules are removed from the drying tunnel. Advantageously, the capsules have been removed at a hardness of approximately 9.5 N (recommendation: 8 to 12 N). The capsule hardness is the force generated by compression of the capsule for a given period of time. The tester is composed of a movable stage attached to a screw mechanism and an upper flat surface punch attached to a strain gauge. The moveable stage applies a continually increasing force to the capsule by controlled rotation of the screw. The capsule is placed between the moveable stage and the punch. The movable stage is manually adjusted until the capsule is in contact with both the stage and upper punch surface. The tester is activated and the stage applies an increasing force by rotation of the screw at a rate of 0.1 mm per second for a total of 20 seconds. The resultant force is measured by a strain gauge attached to the punch. The resultant force is measured in Newton to an accuracy of +/−0.1 Newton, range of operation is 0 to 20 Newton. Capsules might be solvent washed with ethanol to remove excess of lubricants and ease-up the coating after drying.

Inspection

Capsules are inspected for leakage and cosmetic defects after completion of drying. Any defective capsules are removed. Capsules immediately adjacent to capsules on drying trays that have leaked fill solution are segregated and destroyed. Sorting is then conducted to ensure over and under sized capsules are removed prior to packaging. The capsules may be placed into high-density polyethylene (HDPE) bins. A size grading operation could be performed.

Bulk Packaging

The Soft Gelatin Capsules are bulk packed in polyethylene bags (optionally Aluminium bags) which are then placed inside corrugated fibre board carton for transport for enteric coating if off-site.

Enteric Coating

Spray Solution Preparation

The required quantities of triethyl citrate, talc and purified water are homogenized with a Ultra Turrax mixer for at least 5 minutes and then poured into the Eudragit® L30 D-55 dispersion while stirring gently with a propeller stirrer. Finally, the finished spray suspension is poured through a 355 µm sieve. The spraying suspension applied for 7.5 oval soft gelatine capsules manufacture is Eudragit® L30 D-55, talc, triethyl citrate, purified water (133.3/10.00/8.00/156.4).

Coating

The spray suspension is stirred continuously during the coating process. Coating is performed using a 10 L IMA coating pan. The soft gelatine capsule bed (approximately 10,000 soft gelatine capsules) was maintained between 32 and 24° C., the inlet air temperature is 61 to 62° C., the air flow is 125-135 $m^3/h$ and the pan rotation speed is 18 rpm. The spraying rate is approximately 14 to 17 g/min over 118 to 235 minutes (efficient time excluding nozzle and tubing blockages) in order to reach the desired coating level. The coated capsules did not undergo a specific curing step, although the product was allowed to stand overnight.

Enteric coating is usually applied by using a spraying method, for example pan coating or fluidized air bed coating technique.

The final enteric pharmaceutical dosage form can be monolithic or multiparticulate. That means both final dosage form (hardshell capsule, softgel capsule) and intermediate products (pellets . . . ) can be coated. A particular dosage form are a multiparticulate form (coated pellets filled into hardshell capsules) in order to minimize inter-individual variability.

Examples of plasticizers for the enteric coating which can be associated with the acrylic derivatives (such as Eudragit L) are as follow: glycerol, propylene glycol, sorbitol, sorbitol/sorbitan blends, diethylphatalate, dibutylphtalate, dibutylsebacate, triethylcitrate, triacetin, acetylated monoglyceride 9-45, polyethylene glycol . . . .

The formulation according to the present invention has the same therapeutical activity as the oligosaccharide (A) which is contained therein. Therefore the present invention also concerns a formulation according to the present invention or an enteric pharmaceutical dosage form according to the present invention for use as drug.

In case where the synthetic oligosaccharide (A) is a heparin-related oligosaccharide, and in particular a heparin-related pentasaccharide, the present invention also concerns the formulation according to the present invention or an enteric pharmaceutical dosage form according to the present invention for preventing and/or treating venous thromboembolism (phlebitis, deep veins thrombosis, pulmonary embolism) and/or a condition related to blood coagulation disorders as well as for preventing and/or treating arterial thrombosis (acute coronary syndrome, myocardial infarction, stroke).

It also concerns a method for preventing and/or treating venous thromboembolism (phlebitis, deep veins thrombosis, pulmonary embolism) and/or a condition related to blood coagulation disorders as well as for preventing and/or treating arterial thrombosis (acute coronary syndrome, myocardial infarction, stroke) comprising the oral administration of an effective amount of the formulation according to the present invention or of the enteric pharmaceutical dosage form according to the present invention to a patient in need thereof.

Finally it concerns the use of the formulation according to the present invention or of the enteric pharmaceutical dosage form according to the present invention for the preparation of a drug intended for preventing and/or treating venous thromboembolism (phlebitis, deep veins thrombosis, pulmonary embolism) and/or a condition related to blood coagulation disorders) as well as for preventing and/or treating arterial thrombosis (acute coronary syndrome, myocardial infarction, stroke).

The term "therapeutically effective amount" as used herein refers to an amount of an agent according to the present invention needed to treat, ameliorate, or prevent the targeted disease condition, or to exhibit a detectable therapeutic or preventative effect. In general, the therapeutically effective dose can be estimated based on the data available for the parenteral administration of the product in humans.

Effective doses of the compounds of the present invention may be ascertained by conventional methods. The specific dosage level required for any particular patient will depend on a number of factors; including severity of the condition being treated, the general health of the patient (i.e. age, weight and diet), the gender of the patient, the time and frequency of administration, and tolerance/response to therapy. In general, however, the daily dose (whether administered as a single dose or as divided doses) will be in the range 1 to 1000 mg per day, and most usually from 5 to 200 mg per day. Alternatively, dosages can be administered per unit body weight and in this instance a typical dose will be between 0.01 µg/kg and 50 mg/kg, especially between 10 µg/kg and 10 mg/kg, between 50 µg/kg and 2 mg/kg.

An advantage of the compounds of the present invention is that they permit administration to be limited to one, two, three or four times weekly or monthly.

It will be appreciated that any optional feature that has been described above in relation to any one aspect of the invention may also be applicable to any other aspect of the invention.

EXAMPLE 1

Formulation According to the Present Invention

The composition of the formulation according to the present invention is presented in the following table 2:

| % by weight | A | B | F001 | F002 | F002 bis | F003 | F004 | F005 | F006 | F007 |
|---|---|---|---|---|---|---|---|---|---|---|
| Synthetic oligosaccharide | 1.0 | 1.0 | 0.5 | 0.5 | 0.5 | 0.5 | 0.5 | 1.0 | 1.0 | 1.0 |
| Miglyol 812 N | 58.5 | 58.5 | 63.7 | 63.7 | 62.7 | 62.0 | 63.7 | 61.4 | 61.4 | 61.4 |
| Capmul MCM | 23.8 | — | 25.9 | — | — | — | — | 24.8 | — | 24.8 |
| Capmul MCM C10 | — | 23.8 | — | 25.9 | 25.5 | 25.2 | 16.9 | — | 24.8 | — |
| Tween 80 | 9.1 | — | — | — | — | — | — | 9.9 | — | — |
| Brij 30 | — | — | 10.0 | 10.0 | 9.9 | 9.7 | 9.0 | — | — | — |
| Labrasol | — | 9.1 | — | — | — | — | — | — | 9.9 | 9.9 |
| Propylene Glycol | — | — | — | — | — | — | 10.0 | — | — | — |
| H20 | 7.6 | 7.6 | 0.0 | 0.0 | 1.5 | 2.7 | 0.0 | 3.0 | 3.0 | 3.0 |

| % by weight | F008 | F009 | F010 | F011 | F015 | F016 | F018 | F032 | F029 |
|---|---|---|---|---|---|---|---|---|---|
| Synthetic oligosaccharide | 1.0 | 1.0 | 1.0 | 1.0 | 0.5 | 1.0 | 0.5 | 0.99 | 0.9 |
| Miglyol 812 N | — | 61.4 | 61.4 | 61.4 | 61.8 | — | — | — | — |
| Captex 355 | — | — | — | — | — | — | — | 64.36 | 58.56 |
| Captex 1000 | 61.4 | — | — | — | — | 61.4 | 61.8 | — | — |
| Capmul MCM | 24.8 | 22.5 | 22.5 | 22.5 | 25.1 | — | 25.1 | 21.78 | 19.82 |
| Capmul MCM C10 | — | — | — | — | — | 24.8 | — | — | — |
| Tween 80 | — | 9.6 | 9.6 | 9.6 | 9.7 | — | — | 9.9 | 9.01 |
| Labrasol | 9.9 | — | — | — | — | 9.9 | 9.7 | — | — |
| Propylene Glycol | — | 2.5 | — | — | — | — | — | — | — |
| PEG 400 | — | — | — | 2.5 | — | — | — | — | — |
| H20 | 3.0 | 3.0 | 3.0 | 3.0 | 3.0 | 3.0 | 3.0 | 2.97 | 2.7 |
| Ethanol | — | — | 2.5 | — | — | — | — | — | — |
| Aerosil R972 ® Pharma | — | — | — | — | — | — | — | — | 9.01 |
| Aerosil 300 ® | — | — | — | — | — | — | — | — | — |

Sodium fondaparinux has been formulated according to formulations A, F003, F005, F006, F007, F008, F009, F010, F011, F016, F018, F029, and F032. Benzathine fondaparinux has been formulated according to formulation A. The sodium salt of compound 122 has been formulated according to formulation F001, F002, F002 bis and F008. The sodium salt of compound 147 has been formulated according to formulation F003. The sodium salt of compound 675 has been formulated according to formulations F003, F004, F005, F006 and F008. The sodium salt of compound 609 has been formulated according to formulations F003, F005, F008 and F029.

The formulation is prepared by dispersing the active principle ingredient into distilled water at room temperature under stirring (forced vortex). After complete solubilization, the other components of the formulation previously mixed are added at room temperature to obtain a homogeneous emulsion. In the case in which silicon dioxide is present in the formulation, said silicon dioxide is added to the other components of the formulation either before or after the active principle. The emulsion is then stirred for 5 to 15 minutes under forced vortex and/or using a Polytron® homogenizer.

EXAMPLE 2

Digestibility of the Formulation According to the Present Invention

Pancreatic lipase in the presence of colipase catalyses the lipolysis (also termed hydrolysis or de-esterification) of emulsified oils, is a process that results in the production of fatty acids. The rate of fatty acid generation, and thus a measure of the rate of lipolysis can be followed via continuous titration with a pH-stat as described below.

The pH-stat should comprise, for example, a pH-meter, an autoburette and an autotitration unit. These instruments can be obtained from Mettler-Toledo GmbH; Analytical, Schwerzenbach; Switzerland as product number 9301; ID 007612; DL50. The pH-meter should be attached to electrodes suitable for pH-stat titrations (e.g. calomel and glass electrodes from Mettler-Toledo GmbH; DG 115-SC). In addition, a titration assembly unit with a high shear stirrer such as the Mettler Toledo DL50 Titration Assembly equipped with stirrer (e.g. Mettler-toledo GmbH stirrer code 101229) is required. The pH-stat should be set up and operated in accordance with the manufacturer's instructions and calibrated with the certified buffer standards at 37.5° C.+/−0.5° C. immediately prior to use.

The reaction should be performed in a glass thermostated vessel maintained at 37.5° C.+/−0.5° C. This vessel should have an internal diameter of approximately 5 cm and a height of approximately 9 cm. During an experiment the reaction vessel should be placed beneath the titration assembly unit so that the tips of the pH-electrodes and the stirrer are all at least 1 cm beneath the liquid level. It is also necessary to ensure that the contents of the reaction vessel will not escape via leakage or splashing during the course of an experiment.

In order to perform a lipolysis test, the following materials are required:
  calcium chloride
  sodium chloride
  sodium hydroxide pellets
  tris-maleate buffer (e.g. TRIZMA MALEATE from Sigma Aldrich, France)
  standardized sodium hydroxide solution (e.g. 1.0M (N), AVS TITRINORM volumetric solution from VWR, France)
  pancreatin (USP specification) as the source of enzyme activity
  sodium taurocholate (sodium salt, approx. 98%)
  L-α-phosphatidylcholine (L-α-lecithin) type X-E from dried egg yolk The lipolysis tests should be performed in simulated intestinal fluid, pH 6.50, prepared as follow:
Initially prepare 1 L of pH approximately 6.5 buffer containing 50 mM tris-maleate, 5 mM $CaCl_2.H_2O$ and 150 mM NaCl by weighing the following into 1 L volumetric flask and making up to the mark with distilled water:
  0.74 g of $CaCl_2.H_2O$
  8.77 g of NaCl
  11.87 g of tris-maleate
  1.59 g of NaOH Add approximately 0.42 g of sodium taurocholate to 100 ml of the pH 6.5 buffer described above. Gentle stirring will be sufficient to ensure that the bile salt fully dissolves. Warm the resulting solution to approx. 50° C. (with magnetic stirring/hotplate unit) and add approx. 0.12 g of the solid lecithin with continuous stirring. The heat (preferentially under 37° C.) and agitation should be maintained until the lecithin has fully dissolved, typically about 30 minutes.

Place the formulation into the pH-stat reaction vessel and add the 50 ml of simulated intestinal fluid described above into the pH-stat reaction vessel.

The temperature of the system should be maintained at a constant 37.5° C.+/−0.5° C. throughout the lipolysis test. This can be accomplished, for example, by circulating water from a bath with the aid of a suitable thermoregulator.

Move the pH-stat reaction vessel into position beneath the titration assembly. Check that good seals have been achieved and that there is no opportunity for the reaction mixture to escape from the vessel.

Maintain the stirring for 30 minutes under 37.5° C.+/−0.5° C. If the pH changes by more than 0.1 units during this period, then there is a fault with the equipment or set-up procedure and an experiment should not be performed until the problem has been rectified.

Provided the pH has remained stable as described above, the experimental procedure can be continued as follow:

At time 30 minutes, titrate the pH up to precisely 6.50 (e.g. using 1.0M NaOH using the autotitrator). The autotitrator record the volume of titrant dispensed and re-zero the titrant display.

Then, add 0.5 ml of pancreatin solution to formulation and simulated intestinal fluid in the pH-stat reaction vessel. (the pancreatin can be prepared 20 minutes prior to use; see later text for details) Immediately activate the titration system with the end point set at 6.50. Concurrently re-zero the timer and start timing again.

The settings on pH-stat (e.g. titration rate, proportional band) which control the titration speed can be adjusted so that the pH never differs from the target end point (i.e. 6.50) by more than +/−0.05 pH units. At the 60 minute point (i.e. 60 min after the addition of pancreatin solution and the start of the titration) the volume of titrant dispensed is noted.

The lipophilic phase (B) should be approximately 0.5 g in weight and the other formulation compounds should be added in the proportion of the formulation defined. The exact weight of each component added into the pH-stat reaction vessel should be recorded. The molarities of the titrant (e.g. 1.0M NaOH) should be traceable to a primary standard.
Preparation of Pancreatin Solutions:

The pancreatin extracts for use in the lipolysis tests should have an activity of approximately 8 Tributyrin Units (TBUs) per milligram of dry powder0 [Tributyrin Units are defined and their method of determination described, for example, by Patton et al. (Food Microstructure, Vol. 4, 1985, p. 29-41)]

However, pancreatin (USP specification from Sigma Aldrich, France) typically has a lipase activity of 8 TBUs/mg of dry powder.

Lipase solutions can be prepared from pancreatin by mixing the dry powder (e.g. 500 mg) with distilled water (e.g. 2 ml) to produce a 250 mg/ml solution. These solutions, which contain insoluble material, should be prepared in small glass vials (e.g. 5 ml volume) and held for 20 min prior to use at 37.5° C.+/−0.5° C. When this 20 min incubation period has elapsed the solution should be briefly re-mixed and 0.5 ml removed and added to the reaction mixture.

The results are indicated in the following table 3 and have been obtained on formulation containing the sodium salt of Fondaparinux:

| formulation | % lipolysis total after 60 min of digestion | mmoles total free fatty acid released/ g of formulation | mmoles total free fatty acid released after 60 min of digestion/ g of formulation | mmol free $C_{10}$ fatty acid released after 60 min of digestion/ g of formulation |
|---|---|---|---|---|
| A | 59.6 | 3.74 | 2.23 | 0.68 |
| B | 54.6 | 4.11 | 2.24 | 1.23 |
| F007 | 59.66 | 4.22 | 2.52 | 0.8 |

-continued

| formulation | % lipolysis total after 60 min of digestion | mmoles total free fatty acid released/ g of formulation | mmoles total free fatty acid released after 60 min of digestion/ g of formulation | mmol free $C_{10}$ fatty acid released after 60 min of digestion/ g of formulation |
|---|---|---|---|---|
| F006 | 54.63 | 4.11 | 2.25 | 1.24 |
| F008 | 48.04 | 3.98 | 1.91 | 1.28 |

EXAMPLE 3

Bioavailability of the Oligosaccharides, Included into Formulation for Administration According to the Present Invention, after Direct Intra-Duodenal Infusion (DIDI) Administration in Rat Pharmacokinetic Study after Direct Intra-Duodenal Injection:

Direct Intra-Duodenal Infusion (DIDI) has been performed in fasted female Wistar Han rats (175-250 g) to determine the ability of oligosaccharide compounds, in a formulation according to the present invention, to cross the intestinal barrier.

Animals were anesthetized with isoflurane gas in a closed induction chamber and held under anesthesia (3% isoflurane and 2.4 l/min rate) until sacrifice at the end of the experiment. After shaving, a laparotomy was performed and the duodenum exposed. A small pore was created upper the bile duct into the duodenum using a high temperature cautery fine tip. A flexible catheter was inserted into the duodenal lumen through the hole and the upper part of the duodenum was closed and the catheter immobilized by clipping with a forceps. A syringe containing the formulation according to the present invention and diluted as indicated below was placed onto the flexible catheter and the syringe's plunger was slowly depressed releasing the material into the duodenum. Immediately after, a 0.9% NaCl solution was injected (50 µl) to ensure complete compound administration. At this step, peritoneal cavity and skin of the rats were closed using silk suture.

The dose of the oligosaccharide compound according to the present invention to be administrated is 2 mg/kg of body weight or 4 mg/kg of body weight. Therefore, each rat received the quantity of the formulation corresponding to this dosage (i.e. for the dose of 2 mg/kg of body weight, 0.4 mg per rat of 200 g, corresponding to 40 mg of formulation for a formulation containing 1% by weight of the oligosaccharide), diluted extemporaneously at ambient temperature in water for injection with a total volume of administration of 500 µl.

Sometimes, it can be advantageous to first heat the formulation to 37° C. for 15 min under agitation to optimize dilution of the formulation.

Blood samples were collected over a certain period of time (in general 0.25; 0.5; 1; 1.5; 2; 2.5 h) and plasma analyzed as described below.

Quantification of the Compounds in Plasma:

Plasma concentration of the synthetic oligosaccharide (µg compound/mL plasma) was determined using a bioassay based on the factor Xa inhibitory activity of the compounds in the presence of antithrombin (AT). First, AT was added in excess to the plasma sample, allowing 1/1 oligosaccharide/AT complex formation. Factor Xa was then added in excess, and remaining active factor Xa was determined by spectrophotometry at 405 nm using a chromogenic reagent as a substrate. A dose-response curve was established for each compound to be quantified in rat plasma.

Pharmacokinetic Study after Intravenous Administration:

The pharmacokinetics of the studied oligosaccharides after intravenous injection has been investigated to determine the pharmacokinetic parameters of the oligosaccharides, and to allow calculation of their bioavailability after DIDI experiments.

Female Wistar Han rats (175-200 g) catheterized in the external jugular vein were used. The compound was injected (2 mg/kg) as a single bolus administration using a 21 G syringe, followed, immediately after, by a 0.9% NaCl flush (150 µl) to ensure complete compound administration.

Rats were then anesthetized (3% isoflurane, 2.4 l/min) in a closed induction chamber, and held under anesthesia (1.8% isoflurane, 2.4 l/min) until the end of the experiment. At each time point (0.083; 0.25; 0.5; 1; 2; 4; 8 h), blood (200 µl) was collected from the caudal vein, and stored into 3.2% citrated-tubes (0.36% final citrate concentration). Blood plasma was obtained after centrifugation (3,600 g, 10 min, 4° C.) and stored at −20° C. until compound dosing.

Bioavailability Calculation:

The bioavailability of each compound was calculated over a 2 h period of time. The Area Under the Curve from t=0 to t=2 h ($AUC_{0-2}$) was evaluated using the "PK Functions for Microsoft Excel" software. The bioavailability (F) was calculated using the following equation:

$$F(\%) = 100 * (AUC_{0-2} \text{ plasma concentration for DIDI administration}) / (AUC_{0-2} \text{ plasma concentration for intravenous administration})$$

Results:

The results are indicated in the following tables.

The formulation A basis had been developed with various adjustment mainly decreasing the Fondaparinux Na concentration in the formulation-starting from 5 mg in 500 mg and going down to 5 mg in 1250 mg. These formulations variations have been administered at various dose/kg in rats.

| Formulation basis | Drug substance concentration (mg/mg) | Dose delivered (mg/kg) | DIDI |
|---|---|---|---|
| Sodium fondaparinux (without any formulation) | N/A | 2 | 3 ± 2 |
| A - Ratio 1/1 | 5/500 | 2 | 27 ± 23 |
| A - Ratio 1/2 | 5/1000 | 2 | 44 ± 23 |
| A - Ratio 1/2 | 5/1000 | 4 | 37 ± 30 |
| A - Ratio 1/2.5 | 5/1250 | 2 | 21 ± 11 |
| 006 | 5/500 | 2 | 32 ± 20 |
| 007 | 5/500 | 2 | 35 ± 8 |
| 008 | 5/500 | 2 | 31 ± 19 |
| 009 | 5/500 | 2 | 44 ± 19 |
| 010 | 5/500 | 2 | 28 ± 3 |
| 011 | 5/500 | 2 | 29 ± 12 |
| 016 | 5/500 | 2 | 11 ± 1 |

The results indicates that the intestinal absorption of Fondaparinux Na was dramatically increased (from 3% for the plain compound up to 44%) using the formulation according to the present invention. Moreover, increasing the quantity of ingredient above a certain content delivered for a fixed quantity of active substance does not improve absorption in rat model.

| Formulations | DIDI |
|---|---|
| Fondaparinux Benzathine without formulation | 2 ± 1 |
| A - Ratio 1/1 (2 mg/kg) | 30 ± 15 |

The formulations according to the present invention were able to promote intestinal absorption of Fondaparinux independently of the Fondaparinux salt used, whether benzathine (from 2% for the plain compound up to 30%) or sodium (from 3% for the plain compound up to 44%).

| Formulations | DIDI |
|---|---|
| Sodium salt of 122 without formulation | 2.5 ± 1 |
| 001 | 60 ± 19 |
| 002 | 56 ± 16 |
| Sodium salt of 147 without formulation | 1 ± 10 |
| 003 | 41 ± 11 |

The formulations according to the present invention were able to promote intestinal absorption of the oligosaccharides according to WO/2008/041131 (from 2.5% or 1% for the plain compound up to 60% or 41% respectively).

| Formulations | DIDI |
|---|---|
| Sodium salt of 675 without formulation | 1 ± 0 |
| 003 | 15 ± 11 |
| 004 | 57 ± 38 |
| 005 | 13 ± 5 |
| 006 | 10 ± 7 |

The formulations according to the present invention were able to promote intestinal absorption of the oligosaccharides according to WO 01/42262 (from 1% for the plain compound up to 57%).

| Formulations | DIDI |
|---|---|
| Sodium salt of 609 without formulation | 0 ± 0 |
| 002 bis | 51 ± 9 |
| 003 | 28 ± 17 |

The formulations according to the present invention were able to promote intestinal absorption of the oligosaccharides according to WO 2006/067173 (from 0% for the plain compound up to 51%).

EXAMPLE 4

Comparative Examples and Results

The composition of comparative formulation is presented in the following table

| % by weight | C | F019 | F021 | F022 |
|---|---|---|---|---|
| Fondaparinux | 1.0 | 2.1 | 11.1 | 22.5 |
| Miglyol 812 N | 22.3 | — | — | — |
| Miglyol 810 N | — | 17.5 | — | — |
| Cremophor RH-40 | — | 43.4 | — | — |
| Capmul MCM | 4.3 | 26.6 | 55.6 | — |
| Capmul MCM C10 | — | — | — | — |
| Tween 80 | 59.2 | — | — | — |
| Brij 30 | — | — | — | — |
| Brij 78P | — | — | — | 31 |
| Labrasol | — | — | — | — |
| Propylene Glycol | — | — | — | — |
| PEG 400 | — | 3.5 | — | 12.9 |
| H20 | 2.7 | 7 | 33.3 | 33.6 |
| HCL (0.25N) | 10.6 | — | — | — |
| Ethanol | — | — | — | — |

The sodium salt of Fondaparinux was formulated according to formulation C, F019, F021 and F022.

The digestibility of formula C were tested following the procedure indicated in example 2 and were compared with the formulation A and F008 according to the present invention containing the sodium salt of Fondaparinux.

| | Digestion test - 60 min results | | |
|---|---|---|---|
| Formulation | Percentage digested | mmol fatty acid released/g | mmol $C_{10}$ fatty acid released/g |
| A | 59.6 | 2.23 | 0.7 |
| C | 0 | 0 | 0 |
| F008 | 42.5 | 1.7 | 1.1 |

Only the formulations according to the present invention are digestible and therefore could be used orally. This is confirmed by the results of the bioavailability evaluation of formula C after Direct Intra-Duodenal Infusion (DIDI) administration in rat following the procedure indicated in Example 3 which is 0.

An absorbance test has been performed on formula C and F019 and the results obtained have been compared to the results obtained for formulation A and F008 according to the present invention containing the sodium salt of Fondaparinux.

The absorbance test has been performed on a spectrophotometer UV-Visible Varian CARY 3E Instrument at room temperature. Absorbance has been measured at the wavelength $\lambda$ of 400 nm for placebo formulations diluted 100-fold or 1000-fold with distilled water.

The results are as follow:

| | Absorbance test @ 400 nm | |
|---|---|---|
| Formulation | Dilution 1:100 (w/w) | Dilution 1:1000 (w/w) |
| A | 3.33 | 2.06 |
| C | 0.04 | 0.01 |
| F 008 | 2.56 | 1.06 |
| F 019 | 0.03 | 0.02 |

The formulation F019 corresponds to example 66 Table 25 (page 56 line 30) of U.S. Pat. No. 6,761,903

These results show that formula C, which consists in a formulation containing similar components than the ones according to the present invention, but in different quantity in order to match the absorbance characteristics of the formulation of U.S. Pat. No. 6,761,903, are not digestible and there fore not usable orally (the bioavailability of C after Direct Intra-Duodenal Infusion (DIDI) administration in rat using the methodology indicated in Example 3 is 0%). On the contrary, formulation A and F008 according to the present invention which are highly digestible and which have a good bioavailability after Direct Intra-Duodenal Infusion (DIDI) administration in rat do not match the absorbance characteristics indicated as necessary in U.S. Pat. No. 6,761,903.

Finally formula F019 match the absorbance characteristics of the formulation of U.S. Pat. No. 6,761,903, while having low bioavailability after Direct Intra-Duodenal Infusion (DIDI) administration in rat (3±1) using the methodology indicated in Example 3.

These results show clearly that among two parameters potentially dictating formulation efficiency: dispersibility (evaluated by U.S. Pat. No. 6,761,903) and digestibility, the sole parameter digestibility plays a role in the absorption of oligosaccharides.

The bioavailability of the formulations F022 and F021 have been evaluated after Direct Intra-Duodenal Infusion (DIDI) administration in rat following the procedure indicated in example 3 and have been compared with the formulation according to the present invention F008.

The results are indicated in the following table:

|  | Sodium salt of Fondaparinux alone | F008 | F022 | F021 |
|---|---|---|---|---|
| DIDI Rat | 3 ± 2 | 31 ± 19 | 2 ± 2 | 2 ± 2 |

Formulation F022 corresponds to the formulation according to Example 2 h of U.S. Pat. No. 4,656,161. The Example 2 had been selected since it corresponds to Example 1d involving a heparin with Mw of 3000 which is the closest to Fondaparinux Mw. The version h had been selected since this surfactant (Brij 78P) was easily available.

The results show clearly that the presence of a non ionic surfactant is not enough in order to obtain a formulation having a good DIDI bioavailability and therefore which could be administered orally.

Formulation F021 corresponds to Example 2 of U.S. Pat. No. 5,714,477 in which Capmul MCM C10 have been used instead of pure monogycerides. Indeed, pure mono glycerides do not represent a commercially viable option for commercial applications and were not available and portions of di and triglycerides are still reported in Capmul MCM C10 (56.3% mono—38.2% di 5.5% tri). Moreover, the same ratio of Capmul MCM C10 to drug substance was applied. However, the formulation was initially less diluted in water but administration was completed in a volume of 500 µl per rat with approximately 0.4 mg of active delivered per rat (2 mg/kg). Indeed a lower dose of active was delivered since the sodium salt of Fondaparinux is potent at lower dose compared to Fragmin® (16 to 115 mg). Therefore, the end formulation was more diluted in water 0.8 mg/ml whereas the patent example mentions 50 mg/ml.

The results show clearly that the absence of triglyceride has a high impact on the DIDI bioavailability of the formula contrary to what is suggested in U.S. Pat. No. 5,714,477. Therefore the formulation can not contain only mono glycerides or a mixture of mono and diglycerides in order to be administered orally.

EXAMPLE 5

Bioavailability of the Oligosaccharides, Included into a Formulation Containing Silicon Dioxide (F029) According to the Present Invention, after Oral Administration (Per Os) in Dogs Pharmacokinetic Study after Oral Administration in Dog:

Oral administration has been performed into naïve male Beagle dogs (6, 5-8 kg) to determine the bioavailability of oligosaccharide compounds, when delivered in a formulation according to the present invention (namely F029 and F032).

To do so, 7.5 soft gelatine capsules (333 mg) containing a reverse emulsion according to the present invention, with or without silicon dioxide, were manufactured & enterically coated with Eudragit®L 30D-55 according to the procedures described pages 26 to 29. Each capsule contained about 3 mg+/−0.5 of Sodium Fondaparinux. Two capsules as detailed above were individually administered to a group of 6 dogs, by placing them at the back of the animals throat. Swallowing of the capsules was facilitated by administering a small quantity of tap water to each animal. The oligosaccharide dosage to be administered was thus of about 0.8 mg per kg of the animal body weight.

1 mL blood samples were collected over various time points (pre-administration; 0.25, 0.5, 1, 2, 3, 4, 6, 8, 12, 24, 36 and 48 h post-administration) from the saphenous or cephalic veins of unanesthesised animals, into sodium citrate tubes. Blood plasma was collected after centrifugation of the samples (10 minutes, 3000 g, +4° C.) and stored at −20° C. until analysis.

Pharmacokinetic Study after Intravenous Administration:

The pharmacokinetics of the studied oligosaccharide has been investigated after intravenous injection in order to calculate its pharmacokinetic parameters & bioavailability after oral administration.

Dogs were fasted for a period of 14 hours before each intravenous administration, and fed 6 hours after administration (during the kinetics measurement).

For intravenous administration, formulations according to the present invention (with and without silicon dioxide) were administered to the dogs, as a single bolus injection into a peripheral vein (saphenous or cephalic vein) using a plastic syringe pre-rinsed with an aliquot of the oligosaccharide prior to administration.

The dosage of oligosaccharide compound to administer was adjusted to each dog body weight recorded on the day of administration, such that each dog received 0.712 mmol oligosaccharide (Sodium Fondaparinux) per kg of animal body weight.

1 mL blood samples were collected over various time points (pre-administration; 0.083, 0.166, 0.25, 0.5, 1, 2, 3, 4, 6, 8, 12 and 24 h post-administration) from the saphenous or cephalic veins of unanesthesised animals, into sodium citrate tubes. Plasma samples were prepared as detailed above (centrifugation and storage at −20° C. until further analysis).

Quantification of Oligosaccharide Compounds in Plasma:

Plasma concentration of the oligosaccharide compound (µg of compound/mL plasma) was determined by measuring the anti-factor Xa activity of the oligosaccharide using the Stachrom HP kit (Diagnostica Stago). The procedure is fully disclosed in example 3 page 37.

Bioavailability Calculation:

The bioavailability of the oligosaccharide compound was calculated over a 24 h period of time. The Area Under the Curve from t=0 to t=24 h ($AUC_{0-24}$) was evaluated using the "PK Functions for Microsoft Excel" software. The bioavailability (F) was calculated according to this equation:

$F(\%)=100*(AUC_{0-24}$ plasma concentration for Per Os administration$)/(AUC_{0-24}$ plasma concentration for intravenous administration$)$ Results:

a—Oral Administration of a Formulation According to the Present Invention, without Colloidal Silicon Dioxide.

| Dog | Dog weight (kg) | Sodium Fondaparinux (mg) | Sodium Fondaparinux Dosage (mg/kg) | Bioavailability (F %) |
|---|---|---|---|---|
| T51051 | 6.8 | 6.68 | 0.982 | 14.2 |
| T51052 | 8.1 | 6.56 | 0.810 | 84.9 |
| T51053 | 9.0 | 6.26 | 0.696 | 10.7 |
| T51901 | 9.6 | 7.41 | 0.772 | 43.3 |
| T51902 | 7.7 | 7.52 | 0.977 | 17.8 |
| T51903 | 7.1 | 7.64 | 1.076 | 50 |
| | | | | Mean: 37 ± 29 | b—Oral Administration of a Formulation According to the Present Invention, with Colloidal Silicon Dioxide.

| Dog | Dog weight (kg) | Sodium Fondaparinux (mg) | Sodium Fondaparinux Dosage (mg/kg) | Bioavailability (F %) |
|---|---|---|---|---|
| S51901 | 9.5 | 6.84 | 0.720 | 41.9 |
| S51902 | 8 | 6.30 | 0.788 | 20.2 |
| S51903 | 7.3 | 6.71 | 0.919 | 44.7 |
| T51051 | 7.1 | 7.09 | 0.999 | 56.8 |
| T51052 | 8.2 | 6.88 | 0.839 | 35.1 |
| T51053 | 9.1 | 6.94 | 0.763 | 35.3 |
| | | | | Mean: 39 ± 12 |

The results indicate that Sodium Fondaparinux oral bioavailability is greatly improved when a silicon dioxide (Aerosil R972® Pharma) is added to a formulation containing a hydrophilic solvent. Indeed, the variability in bioavailability is reduced by more than 50% when the silicon dioxide is present in the encapsulated emulsion (37%±29 vs 39%±12).

Scale-Up of a Formulation According to the Present Invention, with and without Colloidal Silicon Dioxide.

A scale up production of 7.5 oval soft gelatine capsules (444 mg) containing a reverse emulsion according to the present invention, with or without silicon dioxide, was carried out. The capsules initially contained about 4 mg of Sodium Fondaparinux and were enterically coated with Eudragit®L 30D-55.

| | Batch N° E09523 | Batch N° E09573 |
|---|---|---|
| Formulation per capsule | F008 | F029 |
| Sodium Fondaparinux (mg) per capsule | 4 | 4 |
| Batch size (kg of formulation/number of capsules produced) | 2020/4550 | 1665/3750 |
| Sodium Fondaparinux assay (%) | | |
| beginning of encapsulation | 7.6 | 96.7 |
| end of encapsulation | 0.1 | 94.3 |

The Sodium Fondaparinux assay of each batch was determined using an inverse phase High Performance Liquid Chromatography combined to mass spectrometry. The assay value was calculated based on the initial amount of oligosaccharide present in the formulation used to fill the capsules (4 mg of oligosaccharide=100%).

A sample preparation was performed for each batch on a single capsule in order to quantify Sodium Fondaparinux assay value, upon initiation of encapsulation and at the end of the encapsulation. To do so, the oligosaccharide was extracted into an aqueous solution. The final Sodium Fondaparinux concentration in the working solution was 0.8 µg/ml. The Sodium Fondaparinux concentration in the sample solution was quantified by external calibration using a Sodium Fondaparinux standard solution concentration ranging from 0.2 to 1.4 µg/ml.

The chromatographic analysis was performed on an ODS stationary phase column of 150 mm length, 4.6 mm internal diameter and 3 µm particle size. A gradient of Pentylamine 15 mM/Acetonitrile was used to elute Sodium Fondaparinux. Fondaparinux was detected using an FTMS Orbitrap Exactive mass spectrometer, on ESI negative ion mode.

The results show that the formulation without silicon dioxide (F008) is not stable during the encapsulation process, whereas the formulation with silicon dioxide (F029) is stable. Indeed, the Sodium Fondaparinux assay value of capsules from the batch E09523 is only of 7.6% at the beginning of the encapsulation and reaches a 0.1% value at the end of the encapsulation process. These low assay values show that a phase separation occurred in this formulation, what's more, very rapidly. On the other hand, the Sodium Fondaparinux assay value of capsules from the batch E09573 remains constant and close to 100% throughout the encapsulation process.

Prior to encapsulation, each formulation is stored at ambient temperature in an intermediate storage tank linked to a positive displacement volumetric pump, allowing the filling of the capsules. During the encapsulation process (which can last up to 72 hours), the formulation is submitted to a shear rate by the volumetric pump. A non-stabilized emulsion would become inhomogeneous over storage time, and then be further destabilized due to the shear rate applied during the encapsulation process. This explains the low assay values observed in the batch E09523, both at the beginning and at the end of the encapsulation process. This phenomenon is not observed in the batch E09573; indeed the addition of silicon dioxide has prevented the formation of a phase separation and has thus stabilized the emulsion throughout the entire encapsulation process.

The presence of silicon dioxide is thus required in order to industrially produce homogeneous formulations according to the present invention.

EXAMPLE 6

Particle Size Distribution of Formulations Containing Silicon Dioxide According to the Present Invention, with Various Quantities of Synthetic Oligosaccharide The particle size distribution (PSD) of formulations containing silicon dioxide and various amounts of Sodium Fondaparinux was evaluated by optical microscopy, using Morphology G2 equipment. The compositions of these formulations are presented in the following table:

|  | Sodium Fondaparinux (mg/550 mg) | | | | |
| --- | --- | --- | --- | --- | --- |
|  | 0 | 1 | 2.5 | 4 | 5 |
| compounds | % by weight | | | | |
| Fondaparinux | 0 | 0.18 | 0.45 | 0.72 | 0.90 |
| Captex 355 | 59.09 | 58.98 | 58.82 | 58.66 | 58.56 |
| Capmul MCM | 20.00 | 19.96 | 19.91 | 19.86 | 19.82 |
| Tween 80 | 9.09 | 9.07 | 9.05 | 9.03 | 9.01 |
| Aerosil R972 ® Pharma | 9.09 | 9.07 | 9.05 | 9.03 | 9.01 |
| H2O | 2.73 | 2.72 | 2.71 | 2.71 | 2.70 |

A drop of each formulation was placed on a microscope slide (76×26 mm) to cover around 30×26 mm and 1 mm of thickness. The automated analysis of the emulsion droplets was carried out by configuring the following parameters using the morphology G2 software (version 6.00, ATA Scientific):
  optic selection: ×20
  scan area: 15 mm$^2$
  Threshold: 150 to 160
  filter: circularity≤0.5 and elongation≤0.2
This method allows to measure particles diameter (in µm), as well as their distribution in the sample:
d(v; 0.1), d(v; 0.5), d(v; 0.9) values were measured, where d=particle diameter (in microns) and v=volume of the sample. A d(v; 0.9) value of 8.5 µm means that 90% of the total sample volume comprises particles with a diameter <8.5 µm.
and means that the particle size is below 1 µm, and thus refers to a microemulsion.

| Sodium Fondaparinux (mg/550 mg) | Particle count | d(v; 0.1) | d(v; 0.5) | d(v; 0.9) |
| --- | --- | --- | --- | --- |
| 0 | — | nd | nd | nd |
| 1 | 43 564 | 1 | 1.5 | 8.5 |
| 2.5 | 48 016 | 1 | 2 | 6.2 |
| 4 | 22 066 | 3.5 | 8.2 | 13.8 |
| 5 | 5 589 | 13.5 | 26.5 | 36.6 |

Firstly, this data shows that the addition of small proportions of Sodium Fondaparinux in the aqueous phase of a reverse microemulsion converts the microemulsion into an emulsion. Secondly, an increase of the Sodium Fondaparinux concentration results in an increase of the emulsion particle size distribution (PSD), which in turn can impact the stability of the formulation over time.

Indeed, the higher the PSD, the faster the emulsion droplets aggregate, leading to a "coalescence" of those droplets. This coalescence leads quickly to a phase-separation in the emulsion. Non homogeneous formulations are not desirable as they cannot be homogeneously filled into a final dosage form in order to deliver the exact target dose (4 mg) in compliance with USP specifications (+/−10%) and standard European practices (+/−5%).

As it was demonstrated that silicon dioxide stabilized emulsions throughout the entire encapsulation process (see example 6), it was further evaluated whether this agent could also stabilize these formulations over longer period of times and thus could prevent a phase separation due to the presence of Sodium Fondaparinux (example 7).

EXAMPLE 7

Physical Stability of Formulation Containing Silicon Dioxide According to the Present Invention (F029D)

The particle size distribution of a formulation containing silicon dioxide according to the present invention was evaluated after submitting the emulsion to an "ageing" treatment. Basically, the formulation was stored in glass bottles closed with a polyethylene top and submitted to various temperatures and humidity conditions. This method allows to simulate real life "ageing" conditions of emulsions by accelerating their destabilization process, thus providing a prediction of their shelf-life stability.

Basically, a 3 months-storage at 40° C. and 75% humidity is approximately equivalent to a natural ageing process of 6 months of the emulsion.

A formulation similar to F029 (F029D) was submitted to a storage at room temperature, a storage at 30° C. and 65% humidity, and a storage at 40° C. and 75% humidity. This formulation has the same content as F029 but differs in that Sodium Fondaparinux (dissolved into water) was added after mixing of the other components (namely Captex 355, Capmul MCM, Tween80 and Aerosil R972® Pharma), and then stirred under polytron for 15 minutes (10 000 rpm to 25 000 rpm)

| F029D (room temperature) | Particle count | d(v; 0.1) | d(v; 0.5) | d(v; 0.9) |
| --- | --- | --- | --- | --- |
| t = 0 | 5092 | 13.3 | 24.2 | 33.1 |
| t = 3 days | 5589 | 13.5 | 26.5 | 36.6 |
| t = 17 days | 4760 | 13.4 | 23.8 | 36.3 |

| F029D (30° C./65%) | Particle count | d(v; 0.1) | d(v; 0.5) | d(v; 0.9) |
| --- | --- | --- | --- | --- |
| t = 1 week | 4914 | 13.3 | 22.8 | 34.6 |
| t = 2 weeks | 6763 | 16.2 | 26.6 | 37.0 |
| t = 1 month | 3524 | 13.2 | 23.9 | 33.2 |
| t = 2 months | 3530 | 15.5 | 24.9 | 33.5 |
| t = 3 months | 2500 | 19.1 | 27.8 | 37.0 |

| F029D (40° C./75%) | Particle count | d(v; 0.1) | d(v; 0.5) | d(v; 0.9) |
| --- | --- | --- | --- | --- |
| t = 1 week | 5916 | 13.6 | 24.0 | 34.1 |
| t = 2 weeks | 5068 | 13.5 | 25.4 | 35.5 |
| t = 1 month | 3177 | 17.7 | 26.9 | 37.0 |
| t = 2 months | 3888 | 17.1 | 28.4 | 39.3 |
| t = 3 months | 2338 | 13.1 | 24.1 | 31.7 |

No change of particle size distribution data is reported over time. Indeed, the PSD doesn't vary after a 3 months storage at 30° C. with 65% humidity or at 40° C. with 75% humidity. These results demonstrate that the formulation containing colloidal silicon dioxide according to the present invention is physically stable over time. This stable formulation can thus be homogeneously filled into a final dosage form throughout the manufacturing process.

EXAMPLE 8

Physical Stability of Formulation Containing Various Physical Stabilization Agents Formulations were developed, using other stabilizing agents than hydrophobic silicon dioxides. Those formulations contained approximately:
  60% Captex 355;
  20% Capmul MCM;
  10% of Tween 80;
  and 10% of physical stabilization agent;

Considering that the addition of oligosaccharide impacts the particle size distribution of the formulation and thus its stability, these formulations were initially tested without the presence of oligosaccharide. This allowed to directly evaluate the physical stabilizing capacity of various typical thickeners of lipid based softgel formulations, namely Aerosil 300®, Akosoft 36® (hydrogenated coco-glycerides), and HVO type II (hydrogenated vegetable oil).

Those physical agents have a high melting range and when melted and cooled down during formulation processing, they undergo a nucleation and crystal growth phase creating a network within the lipid system. The formation of this network allows a proper suspension of the particles, which thus results in an homogenous emulsion.

The results showed that these agents, with the exception of Aerosil 300®, were not able to create a network within the current formulation.

A decreased concentration (3%) of Akosoft 36® and HVO was then tested in the formulation according to the present invention. These formulations didn't form a network but were highly liquid, and thus not desirable to orally deliver synthetic oligosaccharides such as heparin or its derivatives. Considering these results, no further development was carried out on formulations with Akosoft 36® or HVO. On the other hand, the formulation containing Aerosil 300® formed a network. 3% and 6% water was thus further added to this formulation to evaluate its stability when submitted to an ageing treatment (storage at 40° C. with 75% humidity).

This formulation exhibited a lower stability than formulation F029. Aerosil 300® is an hydrophilic colloidal silicon dioxide, whereas Aerosil R972®Pharma used in formulation F029 is hydrophobic. The best stabilizing agent to orally deliver synthetic oligosaccharides such as heparin in a formulation according to the present invention is thus a hydrophobic colloidal silicon dioxide.

The invention claimed is:

1. A pharmaceutical formulation intended for oral administration containing a synthetic oligosaccharides containing 3 to 18 monosaccharide units and having a therapeutical activity or a pharmaceutically acceptable additions salt or solvate thereof wherein the formulation contains:
   a) the synthetic oligosaccharide (A) in an amount of up to 5% by weight of the total weight of the formulation,
   b) a lipophilic phase (B) consisting of triglyceride of fatty acids in an amount of 58 to 64% by weight of the total weight of the formulation,
   c) at least one lipophilic surfactant (C) with HLB below 7 consisting of partial esters of polyol and fatty acids in an amount of 10 to 30% by weight of the total weight of the formulation,
   d) at least one hydrophilic surfactant (D) with HLB above 7 in an amount of up to 20% by weight of the total weight of the formulation,
   e) optionally, at least one hydrophilic solvent (E) in an amount of up to 15% by weight of the total weight of the formulation,
   f) between 0 and 30% by weight of the total weight of the formulation of a chemical and/or physical stabilization agent (F), wherein when the formulation is in a form of a reverse emulsion or microemulsion and contains at least one hydrophilic solvent (E), the physical stabilization agent is present and is silicon dioxide.

2. Formulation according to claim 1 wherein the lipophilic phase (B) consists of triglycerides of medium chain fatty acids.

3. Formulation according to claim 1 wherein the hydrophilic surfactant (D) is selected from the group consisting of a polyoxyethylene (20) monooleate, PEG 8 caprylic/capric glycerides, PEG 6 caprylic/capric glycerides, poly(oxyethylene)(4)Lauryl ether and mixtures thereof.

4. Formulation according to claim 1 wherein the hydrophilic solvent (E) is selected from the group consisting of propylene glycol, PEG 400, diethylene glycol monoethyl ether, glycerol triacetate, ethanol, glycerol, dimethylisosorbide, N-methyl-2-pyrrolidone, poloxamers, water and mixtures thereof.

5. Formulation according to claim 1 wherein the lipophilic surfactant (C) consists of a mixture of mono and diglyceride of medium chain fatty acids.

6. Formulation according to claim 1 wherein it contains the hydrophilic solvent (E) and it is in the form of a reverse microemulsion, a reverse emulsion or a micellar solution in oil.

7. Formulation according to claim 1 wherein its extent of digestion after 60 minutes in pancreatin solution containing a pancreatin extract having an activity of approximately 8 Tributyrin Units (TBUs) per milligram of dry powder in distilled water at the dosage of 250 mg/ml at 37.5° C.+/−0.5° C. is such that at least 1 mmol of the total free fatty acid is released/g of the formulation.

8. Formulation according to claim 1 wherein the formulation is homogenous.

9. Formulation according to claim 1 wherein the oligosaccharide is a pentasaccharide.

10. Formulation according to claim 9 wherein the pentasaccharide is a heparin-related pentasaccharide.

11. Enteric pharmaceutical dosage form which contains the formulation according to claim 1, the enteric dosage form being pH dependent.

12. A method for treating and/or preventing venous thromboembolism, comprising administering to a person in need thereof an effective amount of the formulation according to claim 10.

13. A method according to claim 12, wherein:
   the synthetic oligosaccharide (A) is in an amount of up to 1% by weight of the total weight of the formulation,
   the lipophilic phase (B) in an amount of 50 to 70% by weight of the total weight of the formulation,
   the at least one lipophilic surfactant (C) with HLB below 7 consists of partial esters of polyol and fatty acids in an amount of 15 to 30% by weight of the total weight of the formulation,
   the at least one hydrophilic surfactant (D) is up to 15% by weight of the total weight of the formulation,
   the least one hydrophilic solvent (E) is in an amount of up to 10% by weight of the total weight of the formulation, and
   the chemical and/or physical stabilization agent (F) is between 0 and 20% by weight of the total weight of the formulation.

14. A method according to claim 12, wherein said method is for treating acute coronary syndromes, myocardial infarction, or stroke.

15. A method according to claim 12, wherein said composition is in an enteric pharmaceutical dosage form.

16. A formulation according to claim 1, wherein the formulation contains:
   a) the synthetic oligosaccharide (A) in an amount of up to 1% by weight of the total weight of the formulation,
   b) a lipophilic phase (B) consisting of triglyceride of fatty acids in an amount of 58 to 64% by weight of the total weight of the formulation, c) at least one lipophilic surfactant (C) with HLB below 7 consisting of partial esters of polyol and fatty acids in an amount of 15 to 30% by weight of the total weight of the formulation, d) at least one hydrophilic surfactant (D) with HLB above 7 in an amount of up to 15% by weight of the total weight of the formulation, e) optionally, at least one hydrophilic solvent (E) in an amount of up to 10% by weight of the total weight of the formulation, and f) a chemical and/or physical stabilization agent (F) between 0 and 20% by weight of the total weight of the formulation.

17. A formulation according to claim 1, wherein the oligosaccharide is a pentasaccharide in the form of its sodium salt, wherein the lipophilic phase (B) consists of triglycerides of caprylic acid, capric acid, or a mixture thereof, wherein the lipophilic surfactant (C) consists of a mixture of mono and diglyceride of caprylic and/or capric acid, wherein the hydrophilic solvent (E) is propylene glycol, water, or mixtures thereof.

18. A method according to claim 12, wherein the formulation is an enteric dosage form, wherein the enteric dosage form is pH dependent, wherein the thromboembolism is phlebitis, deep-veins thrombosis or pulmonary embolism, and wherein the condition related to blood coagulation disorder and/or for preventing and/or treating arterial thrombosis is acute coronary syndromes, myocardial infarction, or stroke.

19. A method according to claim 13, wherein the formulation is an enteric dosage form, wherein the enteric dosage form is pH dependent, wherein the thromboembolism is phlebitis, deep-veins thrombosis or pulmonary embolism, and wherein the condition related to blood coagulation disorder and/or for preventing and/or treating arterial thrombosis is acute coronary syndromes, myocardial infarction, or stroke.

* * * * *